(12) United States Patent
Sommer et al.

(10) Patent No.: US 7,187,971 B2
(45) Date of Patent: *Mar. 6, 2007

(54) MEDICAL FLUID DELIVERY SYSTEM

(75) Inventors: John L. Sommer, Coon Rapids, MN (US); James A. Coles, Jr., Minneapolis, MN (US); Daniel C. Sigg, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 435 days.

This patent is subject to a terminal disclaimer.

(21) Appl. No.: 10/754,844

(22) Filed: Jan. 8, 2004

(65) Prior Publication Data

US 2004/0143314 A1   Jul. 22, 2004

Related U.S. Application Data

(63) Continuation-in-part of application No. 10/262,046, filed on Oct. 2, 2002, now Pat. No. 7,103,418.

(51) Int. Cl.
*A61M 31/00*   (2006.01)
*A61N 1/05*   (2006.01)

(52) U.S. Cl. ............... 607/3; 607/119; 607/120; 604/21; 604/508

(58) Field of Classification Search ......... 607/119–122
See application file for complete search history.

(56) References Cited

U.S. PATENT DOCUMENTS

| | | | |
|---|---|---|---|
| 3,737,539 A | 6/1973 | Jaeggi et al. | |
| 4,106,512 A | 8/1978 | Bisping | |
| 4,360,031 A | 11/1982 | White | |
| 4,506,680 A | 3/1985 | Stokes | |
| 4,606,118 A | 8/1986 | Cannon et al. | |
| 4,774,951 A | 10/1988 | Osypka | |
| 5,143,090 A | 9/1992 | Dutcher et al. | |
| 5,246,014 A | 9/1993 | Williams et al. | |
| 5,261,419 A * | 11/1993 | Osypka | 607/122 |
| 5,396,902 A | 3/1995 | Brennen et al. | |
| 5,431,649 A | 7/1995 | Mulier et al. | |
| 5,447,533 A | 9/1995 | Vachon et al. | |
| 5,496,360 A | 3/1996 | Hoffmann et al. | |

(Continued)

FOREIGN PATENT DOCUMENTS

WO   WO 98/02040   1/1998

OTHER PUBLICATIONS

Fozzard et al., "New Studies of the Excitatroy Sodium Currents in Heart Muscle", *Circulation Research*, vol. 56, No. 4, Apr. 1985, pp. 475-485.

(Continued)

*Primary Examiner*—Carl Layno
(74) *Attorney, Agent, or Firm*—Carol F. Barry; Girma Wolde-Michael

(57) ABSTRACT

A medical fluid delivery system includes an implantable medical lead and a fluid delivery device; the device is adapted to pass through a proximal port, a lumen and a distal port of the lead. The fluid delivery device includes a tissue piercing distal tip and a pre-formed curve in proximity to the distal tip such that the tip is directed away from a lead fixation element after passing beyond the distal port of the lead.

17 Claims, 22 Drawing Sheets

U.S. PATENT DOCUMENTS

| | | | |
|---|---|---|---|
| 5,531,780 A * | 7/1996 | Vachon | 607/120 |
| 5,807,249 A | 9/1998 | Qin et al. | |
| 5,837,006 A | 11/1998 | Ocel et al. | |
| 5,851,506 A | 12/1998 | Zheng et al. | |
| 5,987,746 A | 11/1999 | Williams | |
| 6,010,526 A | 1/2000 | Sandstrom et al. | |
| 6,052,625 A | 4/2000 | Marshall | |
| 6,086,582 A * | 7/2000 | Altman et al. | 606/41 |
| 6,102,887 A * | 8/2000 | Altman | 604/22 |
| 6,192,280 B1 | 2/2001 | Sommer et al. | |
| 6,296,630 B1 * | 10/2001 | Altman et al. | 604/508 |
| 6,366,819 B1 | 4/2002 | Stokes | |
| 6,567,704 B2 | 5/2003 | Sundquist et al. | |
| 2002/0016622 A1 | 2/2002 | Janke et al. | |
| 2003/0032936 A1 * | 2/2003 | Lederman | 604/507 |
| 2003/0093104 A1 | 5/2003 | Bonner et al. | |
| 2003/0191449 A1 | 10/2003 | Nash et al. | |

OTHER PUBLICATIONS

Gellens et al., "Primary structure and function expression of the human cardiac tetrodotoxin-insensitive voltage-dependent sodium channel", *Proc. Natl. Acad. Sci. USA*, vol. 89, pp. 554-558, Jan. 1992.

Guerrero et al., "Slow Ventricular Conduction in Mice Heterozygous for a Connexin43 Null Mutation", *J. Clin. Invest.*, vol. 99, No. 8, Apr. 1997, pp. 1991-1998.

\* cited by examiner

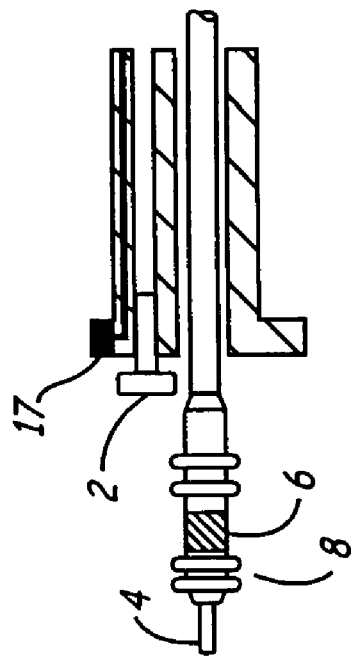
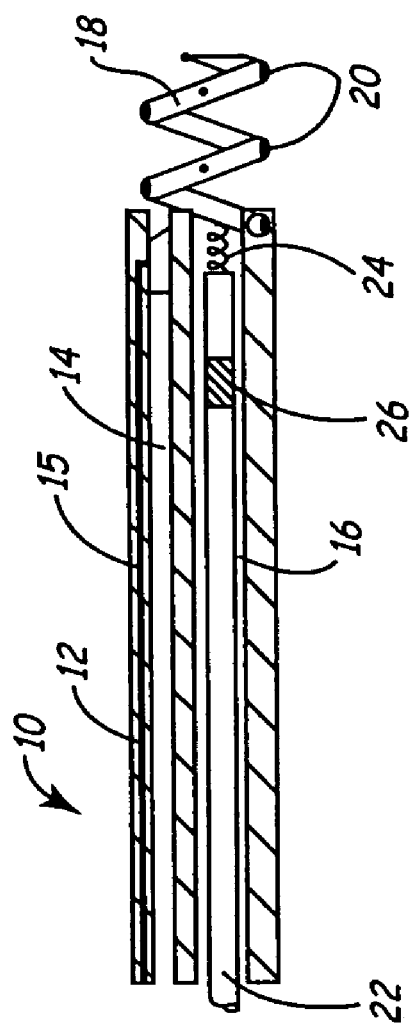
FIG. 2

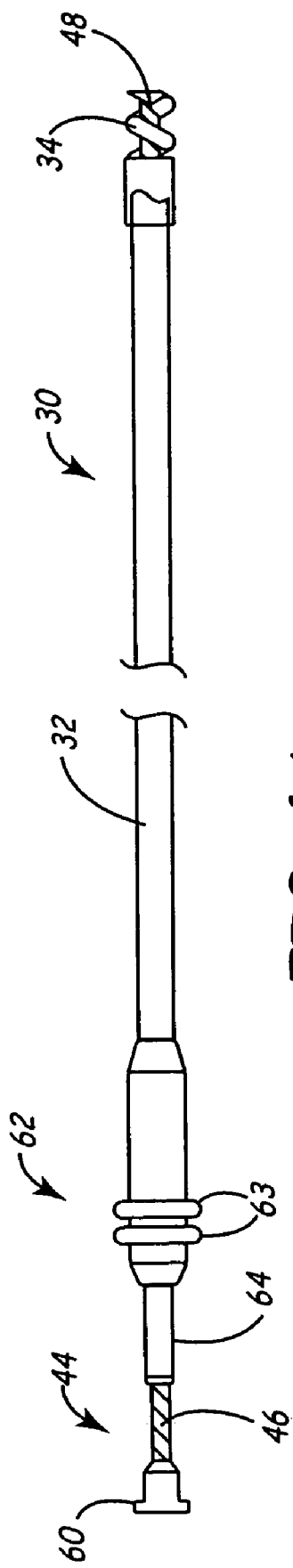
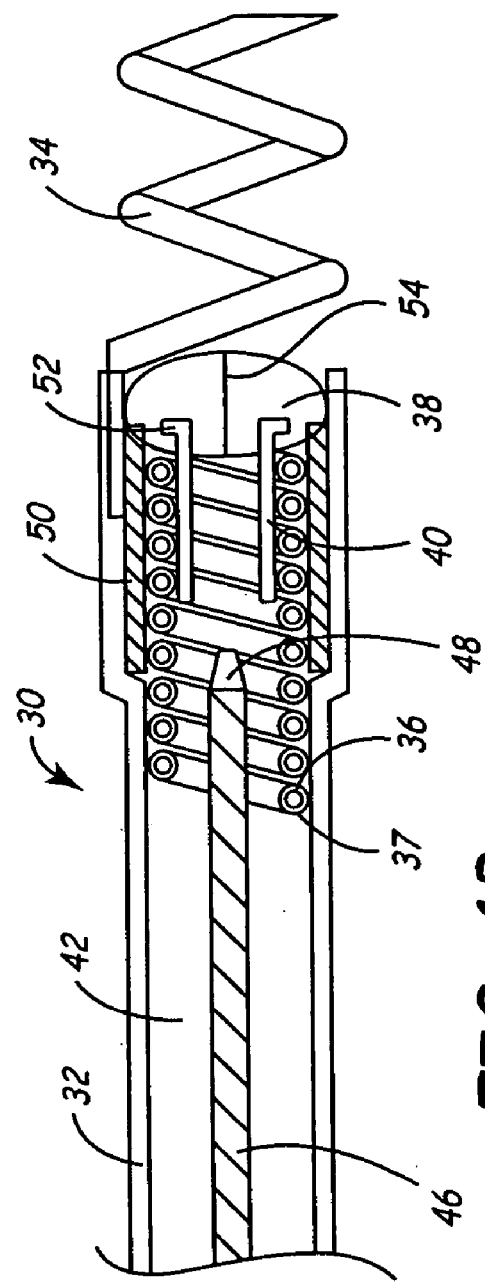
FIG. 4A
FIG. 4B

MEDICAL FLUID DELIVERY SYSTEM

This application is a continuation-in-part (CIP) of application Ser. No. 10/262,046, filed Oct. 2, 2002 now U.S. Pat. No. 7,103,418. The entire content of application Ser. No. 10/262,046 is incorporated herein by reference.

FIELD OF THE INVENTION

The present invention relates generally to implantable medical leads and more specifically to a fluid delivery system for treating tissue in proximity to a lead implant site.

BACKGROUND OF THE INVENTION

Electrical stimulation of excitable body tissue is used as a method for treating various pathological conditions. Therapeutic stimulation generally requires making an electrical contact between excitable tissue and an electrical pulse generator through use of one or more stimulation leads. Various lead systems and various techniques for implanting these lead systems in contact with excitable body tissue, and particularly the heart, have been developed.

In order to achieve cardiac pacing, sensing, cardioversion and/or defibrillation at different locations in the heart, various types of cardiac leads have been developed including epicardial leads, endocardial leads, and coronary vein leads. A transvenous endocardial lead establishes electrical contact between an electrical pulse generator, such as a pacemaker or implantable cardioverter defibrillator, and the endocardial surface of the heart, typically in a right heart chamber. Endocardial leads, and cardiac leads in general, may be held in place by passive fixation mechanisms, such as tines that interact with the ventricular trabeculae, or active fixation mechanisms, such as a helix. A coronary vein lead may be passed through a venous pathway, into the right atrium, through the coronary sinus ostium and ultimately to a location deep in the cardiac veins. Contact is made with the epicardial surface of the left atrium or left ventricle for delivering stimulation or sensing cardiac signals in the left heart chambers. Epicardial leads are also known in the art and generally require a thoracotomy for placement on the epicardial surface of a heart chamber.

The safety, efficacy and longevity of an electrical pulse generator depends, in part, on the performance of the associated cardiac lead(s) used in conjunction with the pulse generator. Various properties of the lead, the electrodes and the tissue interfacing with an electrode will result in a characteristic impedance, stimulation threshold and sensing threshold.

Stimulation threshold is the energy required in a stimulation pulse to depolarize, or "capture," the heart tissue. A relatively high impedance and low threshold is desired to minimize the current drawn from a pulse generator battery in delivering a stimulation pulse. Maximizing the useful life of the pulse generator battery is important since a surgical procedure is required to replace the pulse generator once the battery has reached the end of its useful life.

One factor that can affect the stimulation threshold, particularly during the first several weeks after implantation of a lead, is the natural immunological response of the body to the lead as a foreign object. The presence of the lead activates the immunologic response, which ultimately results in fibrotic encapsulation of the lead and its electrodes. Since fibrotic tissue is not excitable tissue, an elevated stimulation threshold can persist due to the degraded electrical properties of the electrode-tissue interface.

To reduce the inflammatory response, medical leads that elute an anti-inflammatory steroid have been developed. Steroid eluting leads are described in U.S. Pat. No. 4,506,680 issued to Stokes and related Medtronic U.S. Pat. Nos. 4,577,642, and 4,606,118. Steroid eluting leads may require a monolithic controlled release device (MCRD) to contain the steroid and to thereafter slowly leach out the water soluble steroid into the surrounding tissue. A method for applying a steroid directly to the surface of an electrode is disclosed in U.S. Pat. No. 5,987,746 issued to Williams. Advantages of this method include elimination of additional structures for carrying the steroid and the presentation of the steroid directly at the tissue-electrode interface.

One limitation of a steroid eluting electrode or MCRD, however, is that a relatively limited volume of tissue is treated by the eluting drug since the drug is presented only at the endocardial or epicardial surface. Other devices have been proposed which allow the delivery of a drug to a potentially larger volume of tissue by actually penetrating the tissue rather than relying on diffusion of the drug from the tissue surface. Drug delivery catheters may incorporate a drug dispensing needle or helix that penetrates a targeted tissue for delivering a drug or fluid. Catheters that may be used to deliver a fluid or drug into the myocardium are disclosed in U.S. Pat. No. 6,102,887 issued to Altman and U.S. Pat. No. 5,431,649 issued to Mulier et al.

Drug delivery catheters may include an electrode to allow sensing or stimulation of the myocardium. An implantable pacing lead having an active fixation electrode with a stylet introduced, anti-inflammatory drug delivery system is disclosed in U.S. Pat. No. 5,447,533 issued to Vachon et al. A delivery system for delivering a therapeutically effective amount of a genetic material to an identified cardiac location adjacent an atrial or ventricular electrode is disclosed in PCT Patent Publication WO 98/02040 issued to Stokes et al, incorporated herein by reference in its entirety. This delivery system may combine a pacing lead and a delivery catheter. Other implantable leads with drug delivery capabilities are disclosed in U.S. Pat. No. 4,360,031 to White, and U.S. Pat. No. 5,496,360 to Hoffman.

Advancements in gene therapies and cellular modifications through the delivery of proteins, peptides or even cell delivery, such as stem cell delivery, offer opportunities to alter the properties of tissue to further improve the benefit of a delivered stimulation therapy or improve the ability to sense cardiac signals. Genetic or biologic agents may be used to alter ion channel activity or protein expression at the cellular level. Potential benefits include decreased inflammatory response, increased tissue conductivity for reduction of stimulation thresholds or upregulation of ion channels for increasing membrane potentials to allow better sensing. For example, upregulation of ion channels could enhance cardiac P-waves or R-waves allowing them be more easily sensed by a pacemaker or other cardiac monitor. In particular, cardiac fast sodium channels are responsible for the fast upstroke of the action potential in myocardial cells (Fozzard, et al., Circ. Res. 1995, 56:475–485). A human cardiac voltage-dependent sodium channel, hH1, has been cloned, sequenced, and functionally expressed (Gellens, et al., Proc. Natl. Acad. Sci. USA, 1992, 89:554–558). Alteration of myocardial conductivity may be possible through delivery of proteins that alter cellular electrical coupling. The gap junction protein Connexin43 has been found to play an important role in ventricular conduction (Guerrero P A et al., J. Clin. Invest. 1997, 99:1991–1998).

Because locally effective doses of a pharmacologic, genetic, or biologic agent may be toxic when given systemically, it is desirable to provide a method for delivering an agent locally at a targeted tissue site. Drug-eluting electrodes may be limited to treating only a relatively small volume of tissue at an electrode-tissue interface. The pharmacological effect is in part limited by the kinetics of the drug leaving the electrode or lead. Furthermore, because biologic and genetic agents may have a limited shelf life, unique storage requirements such as requiring refrigeration, and may not tolerate sterilization procedures, it is not desirable to package a lead having drug eluting capabilities with the biologic or genetic agent already incorporated therein. Other medical leads having drug dispensing capabilities may require additional components that increase the size, stiffness or complexity of the lead. There is a need, therefore, for a fluid delivery system wherein certain dispensing components, though compatible with an implantable lead, are not integral with the implantable lead so that these components need not be assembled into the lead prior to implant and, once a fluid agent has been delivered, these components, which are no longer needed, may be removed from the patient's body leaving the implanted lead behind.

BRIEF DESCRIPTION OF THE DRAWINGS

FIG. 2 is a side, cut-away view of an alternative embodiment of the guide catheter shown in FIG. 1 in which a fixation member on the guide catheter may also function as an electrode.

FIG. 4A is a plan view of an alternative embodiment of an implantable lead and fluid delivery system including a transvenous medical lead and a fluid delivery device that may be deployed through a lumen of the lead.

FIG. 4B is a side cut-away, view of the distal end of the system of FIG. 4A.

DETAILED DESCRIPTION OF THE INVENTION

Figure 1:
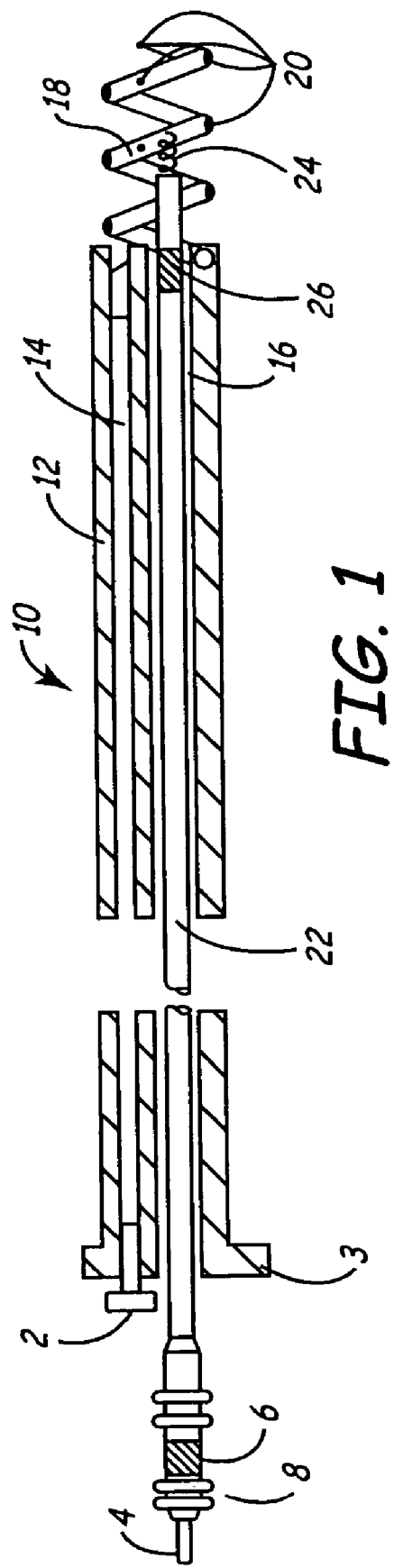
FIG. 1 is a side, cut-away view of an implantable lead and fluid delivery system including a guide catheter having fluid dispensing capabilities and an implantable medical lead.

As described above, the present invention is directed at providing an implantable lead and fluid delivery system in which a fluid delivery device may be used to treat a volume of tissue concurrently with a lead implantation procedure, or at any time post-operatively. After delivering a fluid, the fluid delivery device may be removed leaving the lead implanted at the treated tissue site. FIG. 1 is a side, cut-away view of one embodiment of an implantable lead and fluid delivery system in accordance with the present invention. The system includes a guide catheter 10 having fluid dispensing capabilities. Catheter 10 is provided with a proximal handle 3 and an elongated catheter body 12 having at least two lumens 14 and 16 and is preferably formed from a biocompatible polymer such as polyurethane, silicone, Teflon®, or other acceptable plastic. A fluid-delivery lumen 14 is in communication with an active fixation, fluid dispensing member shown as a hollow fixation helix 18 located at the distal end of guide catheter 10. An active fixation, fluid dispensing member may alternatively be provided as a hollow "fish hook" type member, stake-like member, or any other type of active fixation member that can be provided as a hollow structure having one or more apertures. Hollow fixation helix 18 is provided with one or more apertures 20 through which fluid injected through lumen 14 may exit into a tissue site. Fixation helix 18 is preferably formed from a biocompatible metal, such as stainless steel, in which apertures 20 may be formed by laser drilling. A hollow fixation helix that may be used for fluid delivery is disclosed in the '649 patent issued to Mulier et al., incorporated herein by reference in its entirety, and the WO 98/02040 patent issued to Stokes et al. A fluid fitting 2, such as a Luer lock fitting, may be inserted or mounted at the proximal end of fluid delivery lumen 14 to allow connection of a syringe for injecting fluid into lumen 14.

Catheter 10 may be provided as a steerable catheter having a manipulative handle and steering mechanism, such as a pull wire, to aid in maneuvering catheter 10 through body vessels or organs. Steering mechanisms included in catheter 10 may be embodied as generally described in U.S. Pat. No. 5,396,902, issued to Brennen, et al., for example, or U.S. Pat. No. 5,807,249 issued to Qin, et al., both patents incorporated herein by reference in their entirety.

A lead-delivery lumen 16 is provided for delivering an implantable lead 22 to a desired implant site. The lead-delivery lumen 16 is sized to allow lead 22 to easily pass through guide catheter 10 without undue friction or resistance. Lead 22 is shown as an exemplary bipolar lead having a helical tip electrode 24 located at the distal lead end and a ring electrode 26 spaced proximally from tip electrode 24. In other embodiments, lead 22 may be a unipolar, bipolar, or multipolar lead carrying any combination of tip, ring and/or coil electrodes or other sensors. Lead 22 is shown with an active fixation helical electrode 24 but could also be provided with other types of active fixation electrodes or mechanisms, such as a "fish hook" electrode. Lead 22 may alternatively be provided with a generally spherical, hemispherical or ring-shaped tip electrode with passive fixation mechanisms, such as tines as generally known in the art.

A connector assembly 8 is provided at the proximal lead end with a pin connector 4 and ring connector 6 which are electrically coupled to respective conductors that extend to tip electrode 24 and ring electrode 26. Conductors extending the length of lead 22 may be coiled conductors or cabled or stranded conductors as is known in the art.

During a lead implantation procedure, guide catheter 10 may be passed through a venous pathway into a desired heart chamber until a desired implantation site is reached. A guide wire or electrophysiological mapping catheter, passed through inner lumen 16, could be used for passage of the catheter through the venous and cardiac anatomy to allow access to the targeted tissue. This guide wire or electrophysiological catheter could be steerable and would provide the additional benefit of protecting helix 18 to prevent snagging or entanglement with anatomic structures. Fixation helix 18 is advanced into the myocardial wall by rotating catheter 10 at its proximal end. Catheter body 12 is therefore provided with torsional stiffness adequate to translate rotational force to the distal fixation helix 18. A fluid, which may be a pharmacological, genetic, or biologic agent, may then be injected into drug-delivery lumen 14 such that it is dispersed out of apertures 20 into the tissue surrounding fixation helix 18. A relatively large volume of tissue may be treated by the relatively large helix 18 on guide catheter 10.

Lead 22 may then be passed through lead delivery lumen 16 and implanted at the treated tissue site by advancing helical tip electrode 24 into the tissue. The position of guide catheter 10 is maintained by helix 18 such that lead 22 may be implanted in the same volume of tissue treated by the injection of fluid through helix 18. After implanting lead 22, guide catheter 10 may be removed by rotating catheter 10 in an appropriate direction to remove helix 18 from the tissue site and withdrawing catheter 10 over lead 22. Catheter 10 may be provided as a splittable or slittable catheter such that it may be removed from lead 22 without passing it over connector assembly 8. Alternatively, connector assembly 8 may be provided as a low profile connector assembly sized to allow catheter 10 to be readily passed over assembly 8.

FIG. 2 is a side, cut away plan view of an alternative embodiment of the guide catheter 10 shown in FIG. 1 in which the distal fluid dispensing, fixation member, helix 18, may function as an electrode. In FIG. 2, all identically labeled components correspond to those illustrated in FIG. 1. In FIG. 2, however, fixation helix 18 is shown coupled to a conductor 15 that extends the length of catheter body 12 to a proximal terminal 17 enabling connection to a monitoring device, such as an electrocardiogram monitor. Helix 18 may thus serve as an electrode allowing electrophysiological signals to be sensed and monitored in order to verify that guide catheter 10 is fixed in a desired location. Monitoring of electrophysiological signals may also aid in verifying a short-term pharmacological effect after delivering a fluid through lumen 14 and helix 18.

Figure 3A:
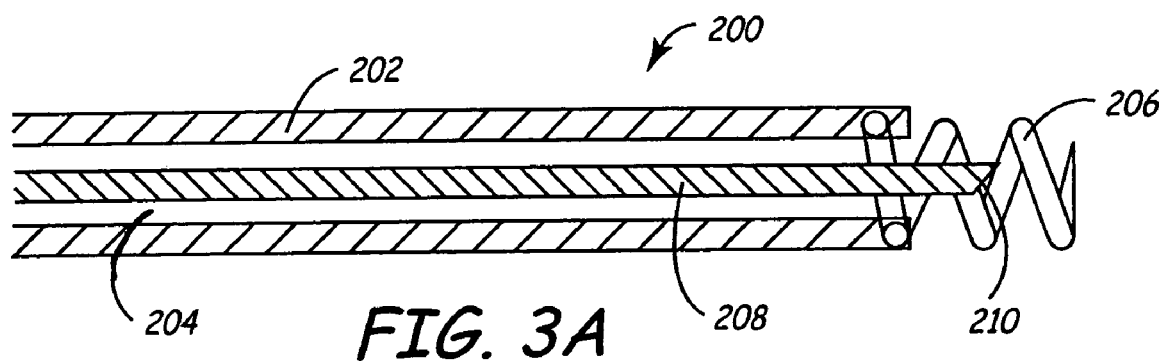
FIGS. 3A and 3B are side, cut-away views of the distal end of an implantable medical lead and fluid delivery system that includes a guide catheter, a fluid delivery device and a medical lead.
Figure 3B:
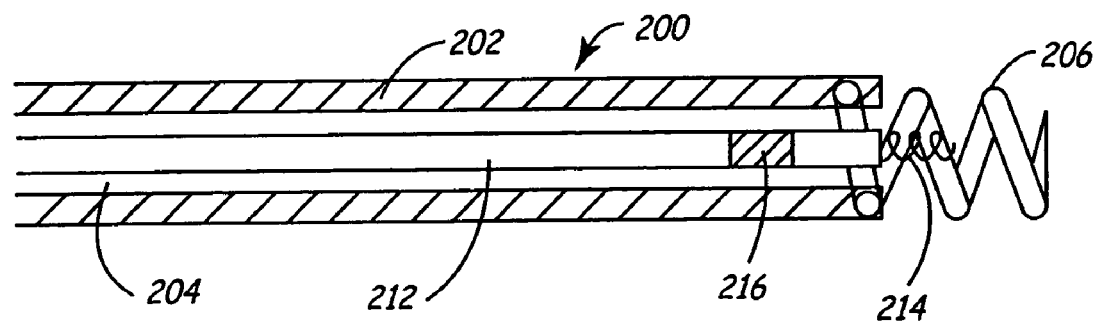

FIGS. 3A and 3B are cut-away plan views of the distal end of an implantable medical lead and fluid delivery system that includes a guide catheter 200, a fluid delivery device 208, and a medical lead 212. FIG. 3A shows a guide catheter 200 having an elongated, tubular catheter body 202 with inner lumen 204. Guide catheter 200 is provided with a fixation member 206, shown in this embodiment as a helix, that allows catheter 200 to be fixed at a targeted implant site. Fixation member 206 may be a solid helix and may function exclusively as a fixation device. Alternatively, fixation member 206 may also function as an electrode as described above with reference to FIG. 2.

A separate fluid delivery device 208 may be advanced through catheter lumen 204 until device 208 exits the distal end of catheter 200. Fluid delivery device 208, which may generally take the form of a hollow needle or stylet, may be tapered at its distal end and is preferably provided with a sharpened or beveled tip 210 such that it may easily pierce the tissue at the targeted implant site. The tip 210 may also take the form of a helix or other shape that may penetrate the tissue to a desired depth and dispense a fluid through one or more apertures to treat a volume of tissue. Once fluid delivery device 208 is advanced into the tissue, a fluid may be injected in the proximal end of fluid delivery device 208 and dispensed into a volume of tissue through tip 210.

Fluid delivery device 208 may also serve as an electrode, alternatively or in addition to helix 206 of catheter 200. Fluid delivery device 208, which may be formed from a conductive metal such as stainless steel, may be provided with an insulating coating, such as a coating of ethylene tetrafluoroethylene (ETFE) or Parylene, except for at distal tip 210. The proximal end of device 208 may be coupled to a monitor such that electrophysiological signals sensed at uninsulated tip 210 may be monitored. Verification that tip 210 is in a desired tissue site, and not in blood or non-excitable tissue, may be made by monitoring electrophysiological signals sensed at tip 210.

After dispensing a fluid into the targeted implant site, the fluid delivery device 208 may be withdrawn from lumen 204 of guide catheter 200 and replaced with an implantable medical lead 212 as shown in FIG. 3B. Lead 212 is shown as an exemplary bipolar lead having an active fixation helical tip electrode 214 at its distal end and a ring electrode 216 spaced proximally from tip electrode 214. Lead 212 may be advanced through lumen 204 and implanted at the treated tissue site by advancing helical tip electrode 214 into the tissue. Guide catheter 200 may then be removed, leaving the electrode 214 implanted in the treated tissue.

FIG. 4A is a plan view of an alternative embodiment of an implantable lead and fluid delivery system. This system includes a transvenous lead 30 and a fluid delivery device 44. The lead 30 has an elongated, tubular lead body 32. Lead body 32 may be formed from a resilient, biocompatible polymer, such as silicone or polyurethane. Lead 30 is shown as a unipolar lead having an active fixation tip electrode 34 located at its distal end, shown as a helical electrode. Lead 30 may alternatively be a bipolar or multipolar lead having, in addition to active fixation tip electrode 32, one or more ring electrodes and/or one or more coil electrodes.

A connector assembly 62 is provided at the proximal lead end to allow connection of lead 30 to an implantable pulse generator or monitoring device. Connector assembly 62 includes a pin terminal 64 that is electrically coupled to tip electrode 48 via a conductor extending the length of lead body 32. Pin terminal 64 is provided as a hollow pin that is in communication with a central lumen of lead body 32. Sealing rings 63 form a fluid-tight seal with the inner surface of a connector port on an implantable pulse generator or monitoring device.

Fluid delivery device 44 is shown inserted into the proximal end of hollow pin terminal 44. Fluid delivery device 44 may take the form of a hollow needle or stylet as described above in conjunction with FIG. 3A. Fluid delivery device 44 includes a hollow shaft 46 sized to pass easily through pin terminal 64 and the lumen of lead body 32 such that distal tip 48 of fluid delivery device 44 may exit the distal end of lead 30. A fluid fitting 60, which may take the form of a Luer lock fitting, is provided at the proximal end of device 44 to allow connection of a syringe for injecting fluid through shaft 46 to be dispensed from tip 48.

FIG. 4B is a side cut-away view of the distal end of lead 30 and fluid delivery device 44. Helical tip electrode 34 is electrically coupled to a conductive sleeve 50, preferably by laser or resistance welding. Conductive sleeve 50 is electrically coupled to a conductor 36. Conductor 36 extends to connector assembly 62 at the proximal end of lead 30 and is coupled to pin terminal 64. Conductive sleeve 50 may be coupled to conductor 36 by crimping conductive sleeve 50 such that it is compressed against conductor 36, which is supported on its internal diameter by internal sleeve 40. In this way, electrode 34 is electrically coupled to conductor 36 and pin terminal 64.

Conductor 36 is preferably a coiled conductor provided with insulation 37. Insulation 37 may be provided as a coating formed from an appropriate insulating material such as polytetrafluoroethylene (PTFE) or ETFE, preferably surrounding each individual filar included in conductor 36. Insulation 37 may alternatively be provided as heat shrink tubing fabricated from PTFE or ETFE as generally described in U.S. Pat. No. 6,052,625 issued to Marshall, incorporated herein by reference in its entirety. Conductor 36 may alternatively be provided as an insulated cabled or stranded conductor, such as the conductor generally disclosed in U.S. Pat. No. 5,246,014 issued to Williams. Insulation 37 may also be provided as a material having a high Young's modulus, such as a high durometer polyurethane or polyimide, to impart additional lead body stiffness to the small diameter lead as generally described in U.S. Pat. No. 6,366,819 issued to Stokes, incorporated herein by reference in its entirety.

Insulation 37 electrically isolates conductor 36 from tip 48 and shaft 46 of fluid dispensing device 44 allowing distal tip 48 to function as a sensing electrode for detecting electrophysiological signals at a tissue site. When tip 48 is used as a sensing electrode, fluid delivery device 44 may also be insulated along the entire length of shaft 46, particularly if conductor 36 is not provided with insulation.

Distal tip 48 remains uninsulated. Insulation on shaft 46 may be provided by an adhesive coating, such as silicone adhesive, or as a tubular sleeve formed from an insulating material such as PTFE, ETFE or Parylene. A conductive clamp, connected to a monitor such as an ECG monitor, may be coupled to fitting 60 at the proximal end of fluid delivery device 44 for observing electrophysiological signals at the site in which the uninsulated tip 48 is in contact. For example, cardiac P-waves or R-waves could be sensed by tip 48.

Lead 30 is preferably provided with a seal 38 to prevent the ingress of body fluids. Seal 38 is generally cup shaped and may be formed from a resilient, biocompatible polymer, such as molded silicone rubber. Seal 38 is shown in FIG. 4B to be molded onto internal sleeve 40, which is preferably formed from a rigid, insulating material such as Delrin®, available from DuPont. Internal sleeve 40 is provided with an annular, laterally extending flange 52. Seal 38 is retained by the interaction of flange 52 and conductive sleeve 50. Seal 38 may be provided as generally described in U.S. Pat. No. 6,192,280 issued to Sommer et al., incorporated herein by reference in its entirety. Alternatively, the seal 38 can be fabricated such that it is entirely contained within a portion of conductor 36 at a point at the distal end of the lead 32 or at a location more proximal. Alternative embodiments of a seal at or near the distal end of a medical lead or medical device that may be adapted for use with the present invention are disclosed in U.S. patent application Ser. No. 20,020,016,622 to Janke et al., and U.S. patent application Ser. No. 20,020,077,685 to Sundquist et al., both of which are incorporated herein by reference in their entirety. Other types of seals for preventing fluid from entering a tubular body may also be used.

During an implantation procedure, lead 30 may be deployed to a desired implant site. Lead 30 deployment may be performed with the aid of a guide wire, stylet, or guide catheter. Helical tip electrode 34 may then be fixed in the tissue at the implant site. If a guide wire or stylet is used, it is removed from lumen 42 after lead 30 is positioned so that fluid delivery device 44 may be advanced through lumen 42. Fluid delivery device tip 48 is preferably sharpened or beveled such that it can easily pierce through seal 38. The fluid delivery device 46 might also be shapeable, allowing it to be used for positioning of the lead 32. Seal 38 may be pre-pierced at line 54 to define a path for the fluid delivery device 44 to pass through. Tip 48 is then further advanced into the implant site. Verification that tip 48 is in a desired implant site may be made by monitoring electrophysiological signals sensed by uninsulated tip 48. If no signal is sensed, tip 48 may not be advanced completely through seal 38 or may not be fully inserted into the tissue site. Once tip 48 is adequately advanced into the implant site, a fluid may be injected through device 44 to treat a volume of tissue in which helical tip electrode 34 is implanted. Fluid delivery device 44 may then be withdrawn and removed, leaving lead 30 implanted with helical tip electrode 34 fixed in the treated tissue.

Figure 5:
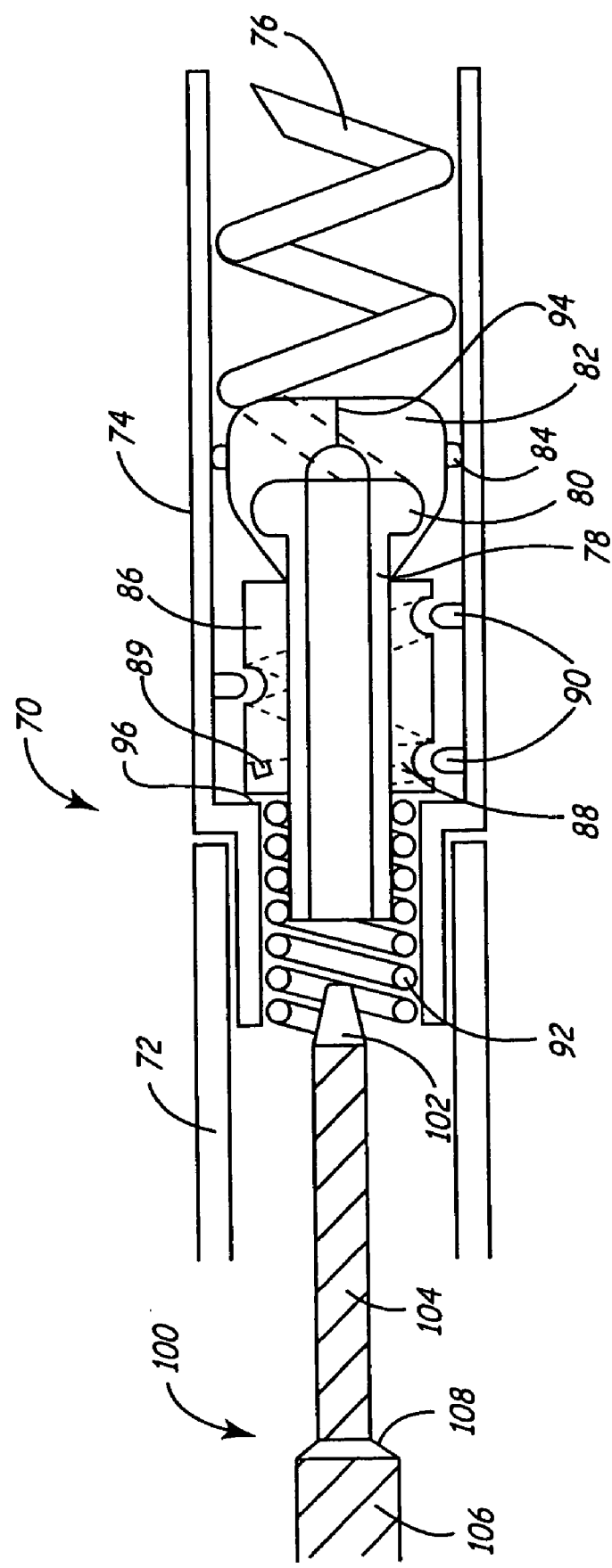
FIG. 5 is an exploded, side, cut-away view of the distal end of an implantable lead and fluid delivery system in which the lead is provided with a retractable fixation member.

FIG. 5 is an exploded, cut-away plan view of the distal end of an implantable lead and fluid delivery system wherein the lead 70 is provided with a retractable fixation member. A lead 70 is provided with a helical tip electrode 76 that may be retracted into an electrode housing 74. Electrode housing 74 is preferably formed from a relatively rigid biocompatible polymer, such as polyurethane. Housing 74 is bonded to an elongated, tubular lead body 72, which may be formed of polyurethane, silicone rubber, or another biocompatible polymer.

Helical tip electrode 76 is mounted on a conductive sleeve 78, which is electrically coupled to a conductor 92. Conductive sleeve 78, which is preferably machined from a conductive metal such as stainless steel, includes a retraction mechanism shown as a threaded barrel 86 that is coaxial with sleeve 78 and located on the outer diameter of sleeve 78. Thread 88, running along the outer surface of barrel 86, acts to engage multiple thread guides 90 mounted on the inner diameter of housing 74. Conductor 92 may be rotated relative to lead body 72 by rotating a connector pin to which conductor 92 is coupled at its proximal end. Rotation of a coiled conductor may be achieved as generally described in U.S. Pat. No. 4,106,512, issued to Bisping, incorporated herein by reference in its entirety. Rotation of conductor 92 causes rotation of sleeve 80 relative to electrode housing 74. Rotation of sleeve 80 causes advancement of helical electrode 76 as threaded barrel 86 is actuated on thread guides 90. A stop mechanism 89 may be provided as a ridge or peg near the proximal end of thread 88 that engages a thread guide 90 to prevent over extension of helical electrode 76. During retraction, threaded barrel 86 will interact with housing 74 at lateral face 96 to prevent over-retraction of helix 76. Alternatively, a stop mechanism may be provided near the distal end of thread 88 to prevent over-retraction of helix 76. A retraction stop mechanism that may be adapted for use in the present invention is disclosed in U.S. Pat. No. 5,837,006, issued to Ocel et al., incorporated herein by reference in its entirety.

Lead 70 is provided with a seal 82, preferably formed of a resilient biocompatible polymer such as silicone rubber, molded to the distal end of the conductive sleeve 78 to prevent ingress of body fluids. Seal 82 may be generally cup shaped and may be pre-pierced at line 94 to guide a fluid delivery device 100 as it passes through seal 82. Seal 82 further includes an annular sealing ring 84, coaxial with seal 82 and extending laterally from the outer diameter of seal 82. Sealing ring 84 interacts with the inner surface of housing 74 to complete a fluid-tight seal of the distal end of lead 70. Sealing ring 84 further acts to center helix 76 within housing 74.

A fluid delivery device 100 is provided which may be generally in the form of a hollow stylet or needle having an elongated shaft 106 extending between a proximal end through which fluid may be injected and a distal tip 102 through which fluid may be dispensed. Distal tip 102 is sharpened or beveled such that it may easily pierce through seal 82 and enter a targeted tissue site. A distal segment 104 of fluid delivery device 100 is provided with a reduced diameter allowing it to extend through conductive sleeve 78 such that distal tip 102 may extend out of housing 74 when helix 76 is extended into a tissue site. Lateral face 108 may act as a mechanical stop by interacting with the distal end of sleeve 78 and thereby control the maximum depth that fluid delivery device 100 is inserted into the targeted tissue site. The outer dimensions of shaft 106 and distal segment 104 and the spacing of lateral face 108 from distal tip 102 may alternatively be dimensioned to provide a stopping interface that interacts with a reduced inner diameter of sleeve 78 or helix 76. Alternatively, the tip of helix 76 may be bent to cross the center axis of helix 76 to act as a stop for fluid delivery device 100. Any of these methods for providing a mechanical stop for fluid delivery device 100 allows the tissue depth at which the fluid is injected to be controlled.

Figure 6:
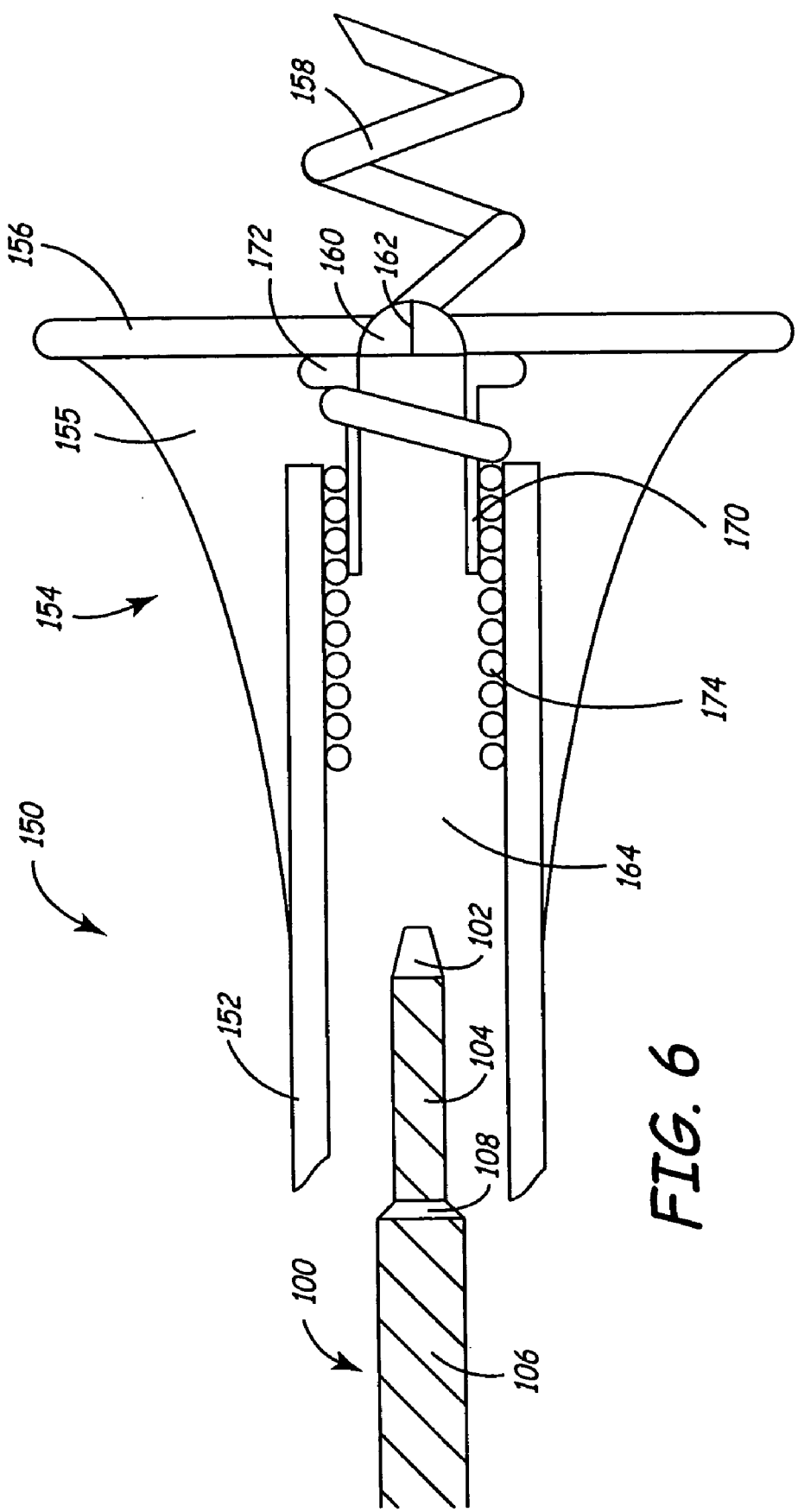
FIG. 6 is an exploded, side, cut-away view of the distal end of an implantable medical lead and fluid delivery system for use on the epicardial surface of the heart.

FIG. 6 is an exploded, cut-away side view of the distal end of an implantable medical lead and fluid delivery system for use on the epicardial surface of the heart. A lead 150 is provided with a lead body 152, an insulating electrode head 154 and an active fixation electrode 158. Electrode 158 is shown as a helical electrode but may also take the form of a "fish hook" type electrode, or any other active fixation electrode. Electrode head 154 includes a tapered body 155 and flange 156, both of which may be formed from silicone rubber and provide a flexible structure for stabilizing the position of lead 150 on the epicardial surface. A tool may be used for implanting lead 150 by attaching to and rotating the electrode head 154 to screw the helical electrode 158 into the epicardium as is generally known in the art. Epicardial leads and tools for implanting epicardial leads are disclosed in U.S. Pat. No. 3,737,539 issued to Bolduc, U.S. Pat. No. 5,143,090 issued to Dutcher, and U.S. Pat. No. 6,010,526 issued to Sandstrom et al., all of which patents are incorporated herein by reference in their entirety. Flange 156 may be reinforced with an embedded netting or mesh material, such as polyester netting. Netting material may optionally be coated with an anti-inflammatory steroid to reduce the inflammatory response at the tissue-lead interface.

Helical electrode 158 is electrically coupled to a conductive sleeve 170, which is further coupled to a conductor 174, shown as a coiled conductor. Conductive sleeve 170 is provided with an annular flange 172. A seal 160 is molded to flange 172 to prevent the ingress of bodily fluids into the lead body lumen 164. Seal 160 may be pre-pierced at line 162 to define a path for fluid delivery device 100 to pass through. Fluid delivery device 100 may correspond to the fluid delivery device shown in FIG. 5 and is shown in FIG. 6 with identically labeled components corresponding to those in FIG. 5. Lateral face 108 may engage with the proximal end of conductive sleeve 170 to control the depth that fluid delivery device 100 is inserted into the tissue.

After implanting lead 150, fluid delivery device 100 may be extended through lead body lumen 164 and seal 160 to dispense a fluid into the tissue surrounding helical electrode 158. Fluid delivery device 100 may then be withdrawn from lumen 164 and removed from the patient's body, leaving lead 150 implanted at the treated tissue site.

Figure 7:
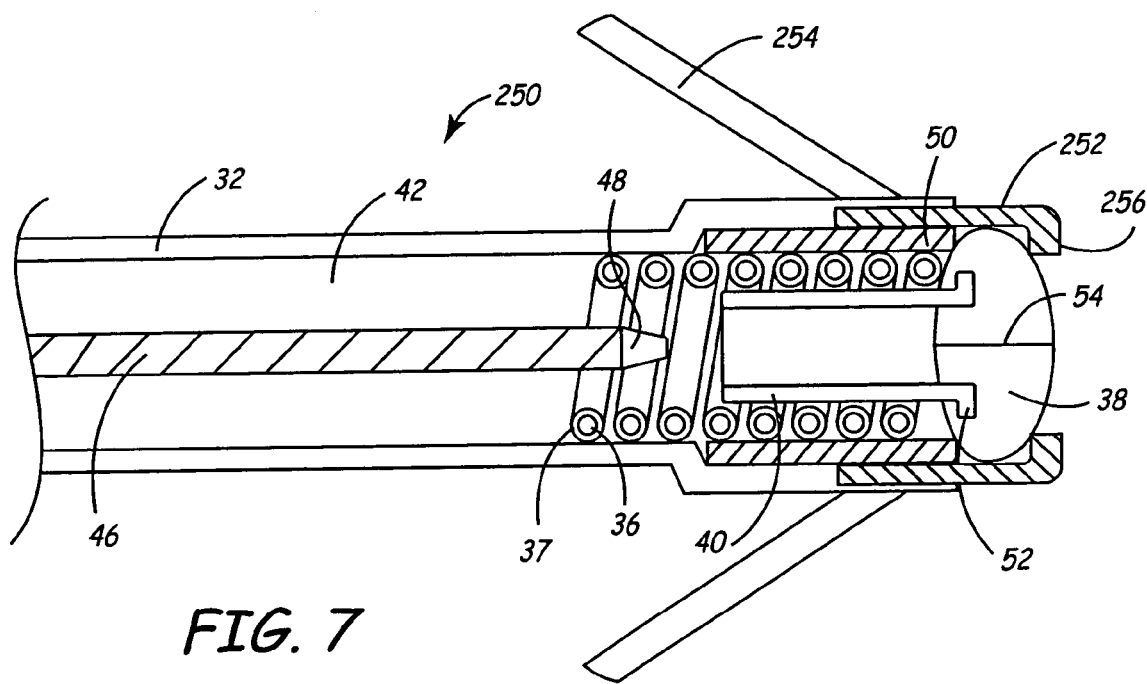
FIG. 7 is a cut-away, side view of the distal end of an implantable medical lead and fluid delivery system wherein the medical lead is provided as a transvenous lead having a passive fixation mechanism.

FIG. 7 is a cut-away, side view of the distal end of an implantable medical lead and fluid delivery system wherein the medical lead is provided as a transvenous lead having a passive fixation mechanism. In this embodiment, all identically labeled components correspond to those illustrated in FIG. 4B, however, in this case, in place of an active fixation electrode at the tip of the lead 250, a ring electrode 252 is provided. Ring electrode 252 is electrically coupled to conductive sleeve 50, which is further coupled to insulated conductor 36 as previously described with reference to FIG. 4B. To stabilize the implanted position of lead 252, passive fixation members 254 are provided, which may take the form of tines as is generally known in the art. Seal 38 may be molded onto internal sleeve 40 as described previously and forms a fluid-tight seal with the inner diameter of ring electrode 252. Ring electrode 252 may be provided with an annular lip 256 which may act to retain seal 38.

Figure 8:
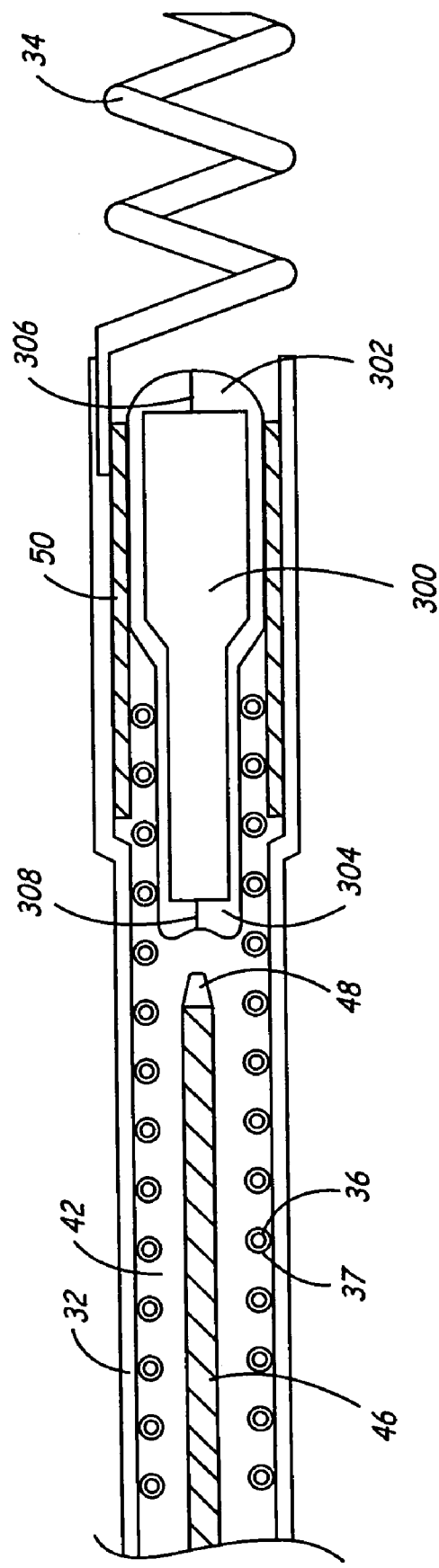
FIG. 8 is side, cut-away view of the distal end of an implantable medical lead and fluid delivery system wherein the medical lead is further provided with a fluid reservoir for holding a pharmaceutical, genetic or biologic agent and allowing the agent to elute into adjacent body tissue over time.
Figure 9:
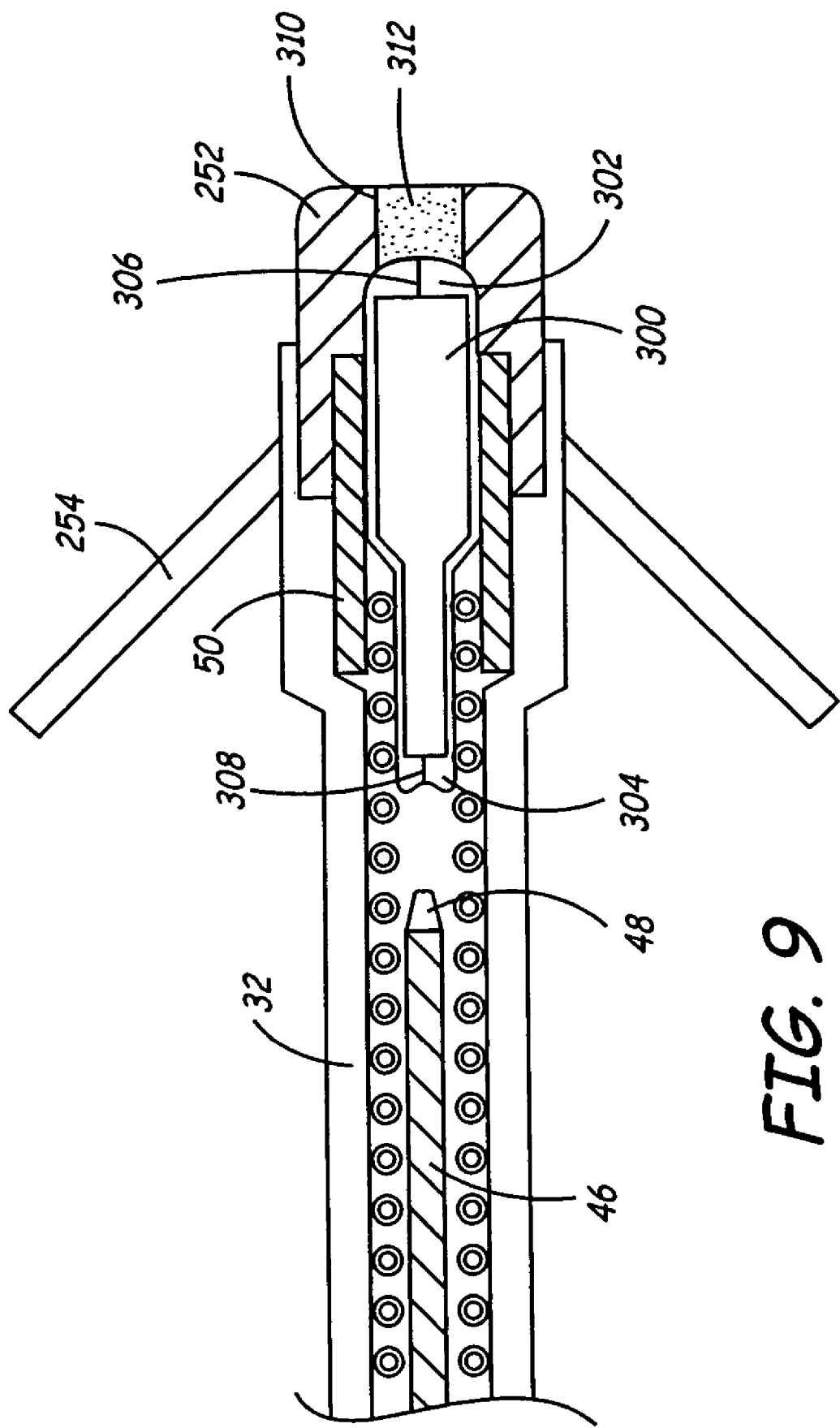
FIG. 9 is a side, cut-away view of the distal end of an implantable medical lead and fluid delivery system wherein the medical lead is provided as a transvenous lead having a passive fixation mechanism and a fluid reservoir.

FIGS. 8 and 9 are side, cut-away views of the distal end of an implantable medical lead and fluid delivery system wherein the medical lead is further provided with a fluid reservoir for holding a pharmaceutical, genetic or biologic agent and allowing the agent to elute into adjacent body tissue over time. A body implantable lead having a cavity suitable for retaining a drug is disclosed in U.S. Pat. No. 4,506,680 issued to Stokes, incorporated herein by reference in its entirety. A combined catheter and reservoir, useful for applications involving delivery of genetic material, is disclosed in the previously cited PCT Patent Publication WO 98/02040.

The lead shown in FIG. 8 corresponds to the lead of FIG. 4B having a helical tip electrode 34 electrically coupled to stem 50 which is further coupled to an insulated conductor 36. In addition to or in place of a seal at or near the distal end of the lead, a fluid reservoir 300 is located near the distal end of the lead. A fluid delivery device in the form of a hollow stylet or needle, having a shaft 46 and sharpened tip 48, may be used to fill reservoir 300 with a fluid. Reservoir 300 preferably includes a seal 304 covering a proximal opening to reservoir 300 and a seal 302 covering a distal opening to reservoir 300. Fluid delivery device tip 48 pierces through the proximal seal 304, which may be pre-pierced at line 308 and may be provided with a concave proximal surface to guide tip 48 to reservoir 300 and through seal 302. Fluid may then be injected into reservoir 300, and the fluid delivery device may be removed. The pharmaceutical, genetic, or biologic agent will elute from reservoir 300, through distal seal 302, into the adjacent tissue over time.

Fluid reservoir 300 may be formed from silicone rubber or alternatively polyurethane or another elastomer. The seals 302 and 304 are preferably formed from silicone rubber. Seal 304 may be provided as a less permeable material than seal 302 to prevent blood or bodily fluids from entering the lead body lumen 42 while still allowing a pharmaceutical, genetic or biologic material to elute through seal 304. The reservoir 300 may be provided as a micro-osmotic pump. For example reservoir 300 may optionally contain a salt-loaded silicone material, which would swell over time as salt is replaced by water, or another polymeric material capable of swelling upon exposure to body fluids. Such swelling would aid in "pumping" a fluid agent out of reservoir 300.

Optionally, the fluid delivery device may be further advanced through distal seal 302, which may be pre-pierced at line 306. The fluid delivery device may then be inserted into the tissue in which electrode 34 is implanted to deliver a bolus of fluid directly to the tissue site, at a desired depth within the tissue. The fluid delivery device may then be withdrawn into reservoir 300 and used to fill reservoir 300 to allow a pharmaceutical, genetic or biologic agent to elute slowly over time into the adjacent tissue. In this way, local treatment of a volume of tissue may be performed by delivering a bolus of fluid directly into the tissue, or allowing the agent to elute from reservoir 300 over time, or both. Furthermore, one or more fluid agents may be delivered directly into the tissue site, and another fluid agent may be used to fill reservoir 300 and elute over time allowing the volume of tissue in which electrode 34 is implanted to be treated by at least two different pharmaceutical, genetic or biologic agents over different time courses.

A fluid reservoir for storing a fluid agent that will elute over time may also be included in other embodiments of medical lead and fluid delivery systems. FIG. 9 is a cut-away, side view of the distal end of an implantable medical lead and fluid delivery system wherein the medical lead is provided as a transvenous lead having a passive fixation mechanism and a fluid reservoir. The system shown in FIG. 9 is similar to the system shown in FIG. 7, and identically labeled components correspond to those shown in FIG. 7. However, in FIG. 9, the transvenous lead is shown having a fluid reservoir 300, similar to the reservoir described above in conjunction with FIG. 8. Ring tip electrode 252 is provided with a central bore 310 that may be filled with a porous material through which a pharmaceutical, genetic or biologic agent eluting out of reservoir 300 may pass to reach adjacent body tissue. A porous elution path may be formed from sintered metal structures as disclosed in the above incorporated '680 patent. Alternatively central bore 310 may be left open, as shown previously in FIG. 7, to allow a fluid delivery device to be passed through tip electrode 252 to inject fluid directly into the tissue as well as providing an open elution pathway.

In some cases, it may be desirable to deliver a therapeutic fluid at a time after the lead implantation procedure. For example, pharmacological, genetic or biological treatments may need to be repeated at certain intervals over time post-operatively in order to achieve a desired therapeutic effect. A situation may also arise requiring a chronically implanted lead to be repositioned due to dislodgment or declining stimulation or sensing performance. It may be desirable to treat the tissue at the new implant site at the time the lead is repositioned. On the other hand, factors that may be causing poor lead function, such as poor tissue conductivity or low membrane potential signals, may be improved by treating the tissue at the chronic lead implant site with a fluid agent, thereby avoiding the need for lead repositioning.

Figure 10:
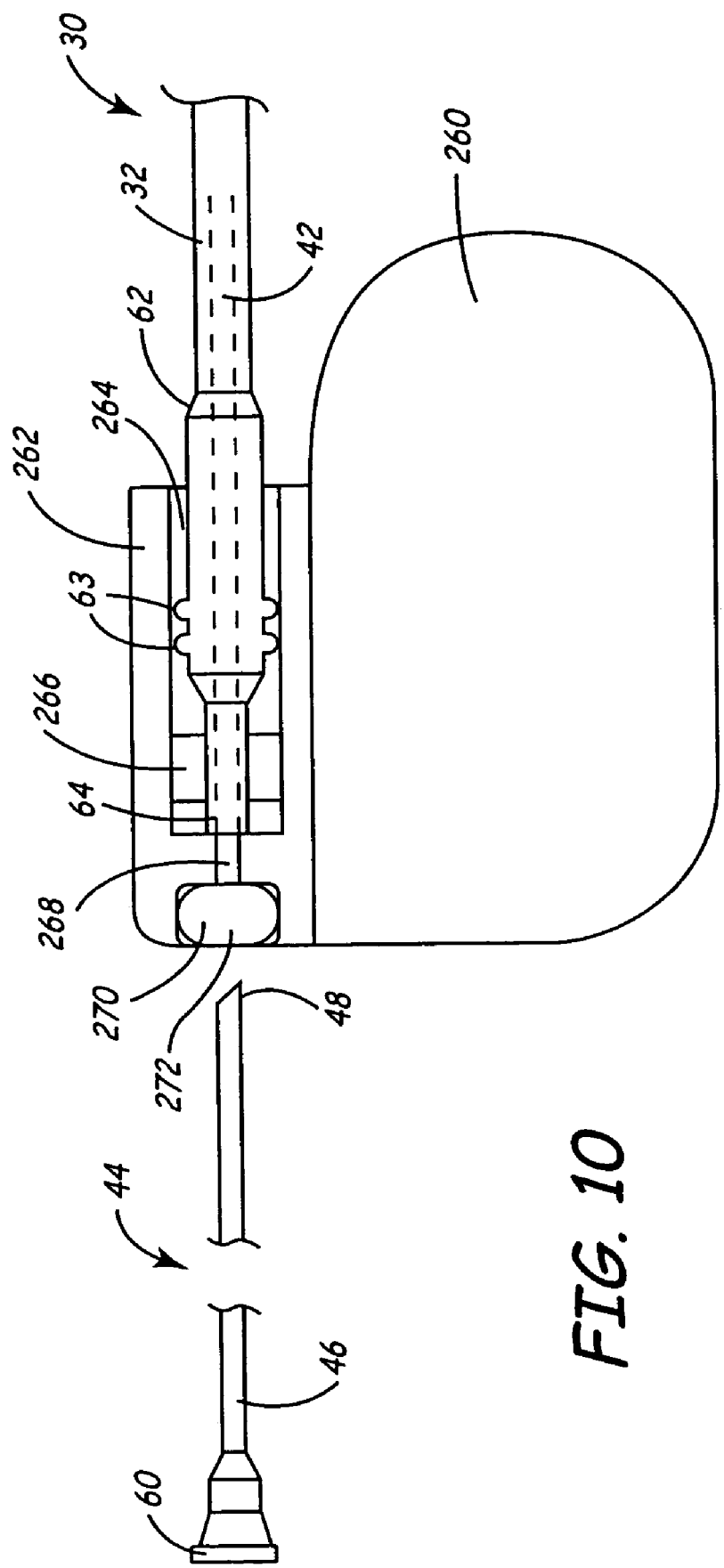
FIG. 10 is a plan view of an implantable lead and fluid delivery system that may be used to deliver a fluid agent to a lead implant site post-operatively.

FIG. 10 is a plan view of an implantable lead and fluid delivery system that may be used to deliver a fluid agent to a lead implant site post-operatively. In this embodiment, lead 30 corresponds generally to that shown in FIG. 4A, and all identically labeled components correspond to those illustrated in FIG. 4A. In FIG. 10, connector assembly 62 at the proximal end of lead 30 is inserted into a connector bore 264 of a connector block 262 provided on a medical device 260, which may be a pacemaker or implantable cardioverter defibrillator, or other type of implantable pulse generator or electrophysiological monitor. Pin terminal 64 is electrically coupled to terminal 266 of connector block 262 to provide electrical connection between lead 30 and device 260. The lumen 42 (indicated by dashed line) of lead body 32 that is continuous with hollow pin 64 communicates with a lumen 268 within connector block 262. Lumen 218 may be accessed through access port 272, which is preferably sealed against body fluids by a grommet 270. Fluid delivery device 44, which may generally correspond to the fluid delivery device described in conjunction with FIG. 4A, may be inserted through access port 272 and grommet 270 such that it may be passed through lumen 268, hollow pin terminal 64 and lead body lumen 42. Fluid delivery device 44 may then exit the distal end of lead 30 until it penetrates the tissue at the lead 30 implant site, as described previously. Once penetrated to a desired depth, fluid may be delivered through fluid delivery device 44. Fluid delivery device 44 may then be removed. Additionally or alternatively, fluid delivery device 44 may be used to refill a fluid reservoir that may be provided near the distal lead end as described in conjunction with FIGS. 8 and 9.

Access port 272 may be exposed during a minor surgical procedure by making a small skin incision at the site that device 260 is implanted. In this way, a volume of tissue at the lead implant site may advantageously be treated using a fluid delivery device at any time post-operatively without performing major surgery or catheterization procedures.

Figure 11:
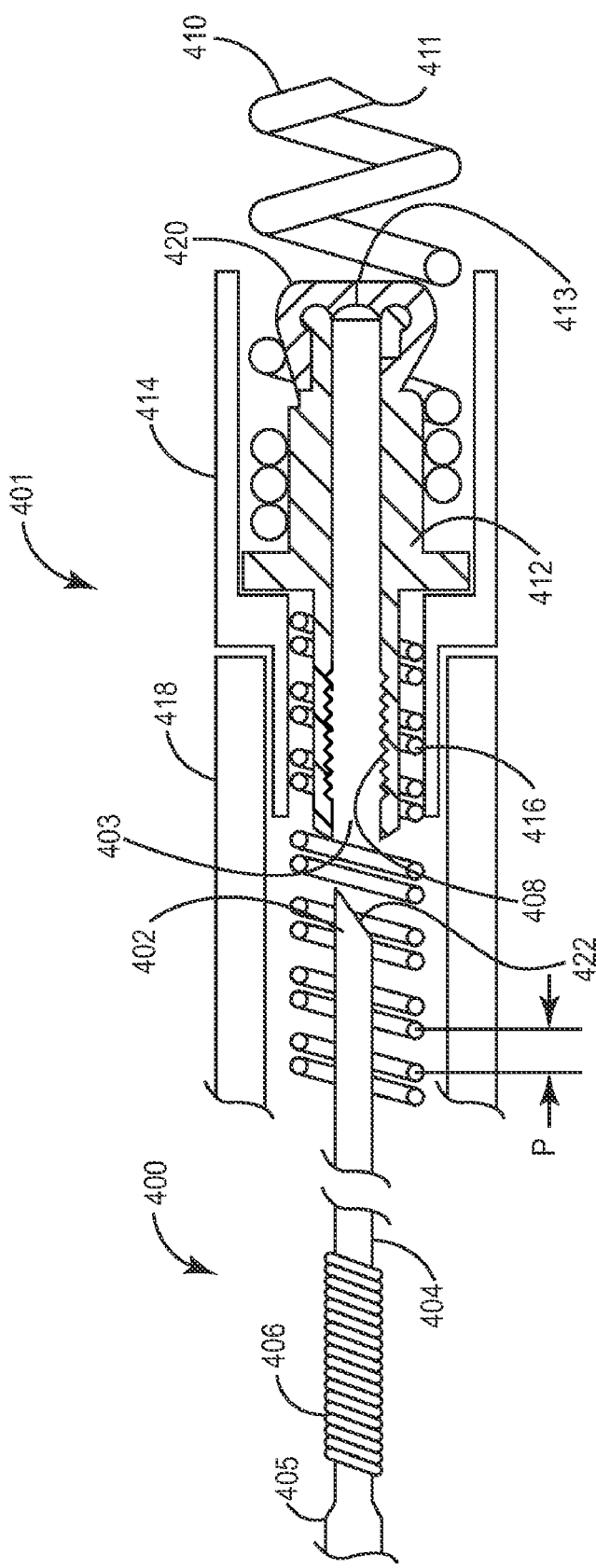
FIG. 11 is a sectional view of a distal portion of a fluid delivery system according to an alternate embodiment of the present invention.

FIG. 11 is a sectional view of a distal portion of a fluid delivery system according to an alternate embodiment of the present invention. FIG. 11 illustrates the system including an implantable medical lead 401 and a hollow fluid delivery device 400 having a piercing distal tip 402; lead 401 includes a lumen 403 adapted to engage device 400 and having a proximal port, e.g. proximal port 513 shown in FIG. 13A, and a distal port 413, formed in a seal 420, through which device distal tip 402 is advanced in order to deliver a fluid into a tissue site. FIG. 11 further illustrates lead 401 including a fixation element 410 positioned in proximity to distal port 413 and coupled to a sleeve 412 within a housing 414 which is in turn coupled to a coiled conductor 416 extending to a proximal end (not shown) of lead 401 within a lead body 418. Device 400, according to some embodiments, is formed of a flexible and elastic rigid or semi-rigid material, either plastic or metallic, being biocompatible and flexible enough to pass through implanted lead 401 without dislodging fixation element 410.

According to embodiments of the present invention, a fixation element, for example element 410, is adapted to secure the lead to a tissue site such that distal port is in proximity to the tissue in order to accommodate passage of device tip 402 into the tissue. In the embodiment illustrated in FIG. 11, electrode sleeve 412 includes a female thread 408 and device 400 includes a male thread 406 to form a threaded interface between lumen 403 and device 400 as a means for adjusting a position of device tip 402 with respect to distal port 413; device tip 402 may thus be advanced through distal port 413 by rotating device 400 at a proximal end and may be retracted by rotating device 400 in an opposite direction. Male thread 406 is formed along a distal portion 404 of device 400 at a selected distance from device tip 402 such that when threaded surfaces 406 and 408 are fully engaged, device 400 is extended a desired distance beyond distal port 413; according to one embodiment, the desired distance is also beyond a distal end 411 of fixation element 410.

According to one embodiment of the present invention, full engagement of threaded surfaces 406 and 408 acts as a stop to limit a maximum distance between device tip 402 and distal port 413 of lead 401; according to an alternate embodiment an enlarged diameter 405 of device 400 acts as a stop. Furthermore, initial contact of male thread 406 with female thread 408 as device 400 is advanced into lead 401 provides tactile feedback which may act as an indicator that device tip 402 is in proximity to distal port 413. Controlled advancement of device tip 402 into adjacent tissue may then be achieved by rotating device 400 with respect to lead 401. The depth that tip 402 is advanced is controlled by the number of rotations performed. A proximal end (not shown) of device 400 may be calibrated to indicate distances that tip 402 is advanced out of the distal end of lead 401.

According to some embodiments, if fixation element 410 also functions as an electrode, sleeve 412 is formed from a conductive material to provide electrical coupling between element 410 and conductor 416; in these cases, device 400 may be provided with an insulating layer, such as a Parylene coating, and male thread 406 may be formed from a durable, non-conductive material such as a fluoropolymer, to electrically insulate device 400 from electrode 410 and conductor 416. According to further embodiments, such an outer layer is also lubricious facilitating smooth passage of device 400 through lead lumen 403.

FIG. 11 further illustrates coiled conductor 416 formed of at least one wire filar including a pitch p and device tip 402 including a beveled end 422; according to some embodiments of the present invention an inner surface of coiled conductor 416 forms a portion of lumen 403 and pitch p of coiled conductor 416 is adapted to prevent beveled end 422 from catching in coiled conductor 416 as it passes through lumen 403. According to one embodiment beveled end 422 is formed at an angle between approximately 22 degrees and approximately 30 degrees.

Figure 12:
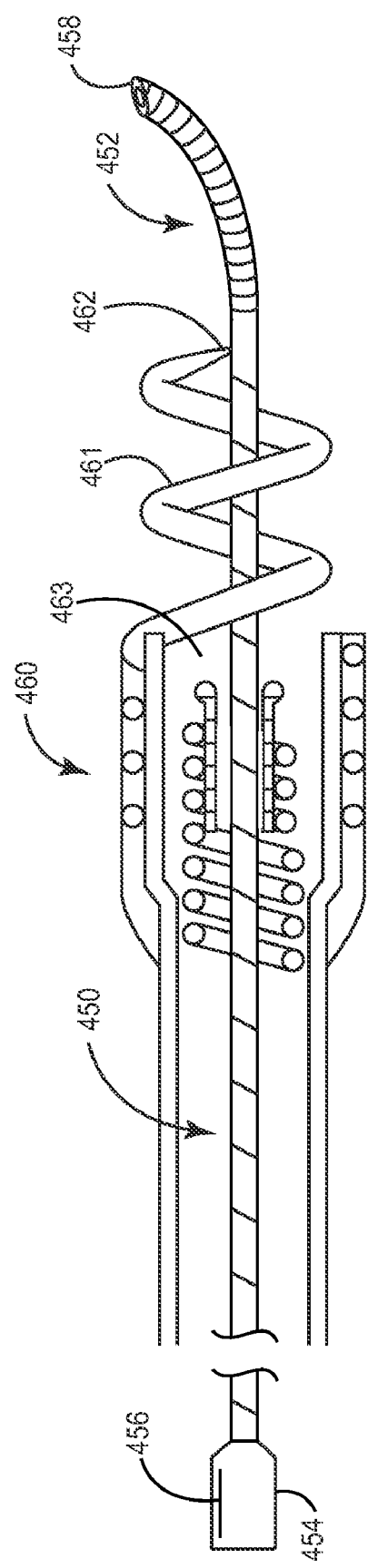
FIG. 12 is a sectional view of a fluid delivery system according to yet another embodiment.

FIG. 12 is a sectional view of a fluid delivery system according to yet another embodiment. FIG. 12 illustrates a hollow fluid delivery device 450 engaged within a lumen 433 of an implantable medical lead 460 and including a tissue piercing distal tip 458 and a preformed curve 452 positioned in proximity to distal tip 458. According to the illustrated embodiment, as device 450 is extended out of a distal port 463 and past a fixation element 461 of a medical lead 460 as shown here, or alternatively extended from a lumen of a guide catheter as described in conjunction with FIG. 1, pre-formed curve 452 becomes un-restrained to direct distal tip 458 away from fixation element 461 in a lateral direction. Although FIG. 12 illustrates preformed curve 452 positioned distal to a distal end 462 of fixation element 461, according to alternate embodiments device tip 458 may be directed in between turns of fixation element 461 to protrude laterally from element 461 in a position proximal to distal end 462.

Hollow fluid delivery device 450 may be formed from a super-elastic material, either metallic or polymer, or from a shape memory alloy; examples of each include NiTi alloys known to those skilled in the art. In some embodiments, a guide wire (not shown) may be inserted through the hollow device 450 to maintain a straight geometry as device 450 is advanced through lead 460, and, in other embodiments, the shape change may be induced by temperature or electrical activation of pre-formed curve 452 formed by a shape memory material after it is advanced out of the distal port 463 of lead 460.

Figure 13:
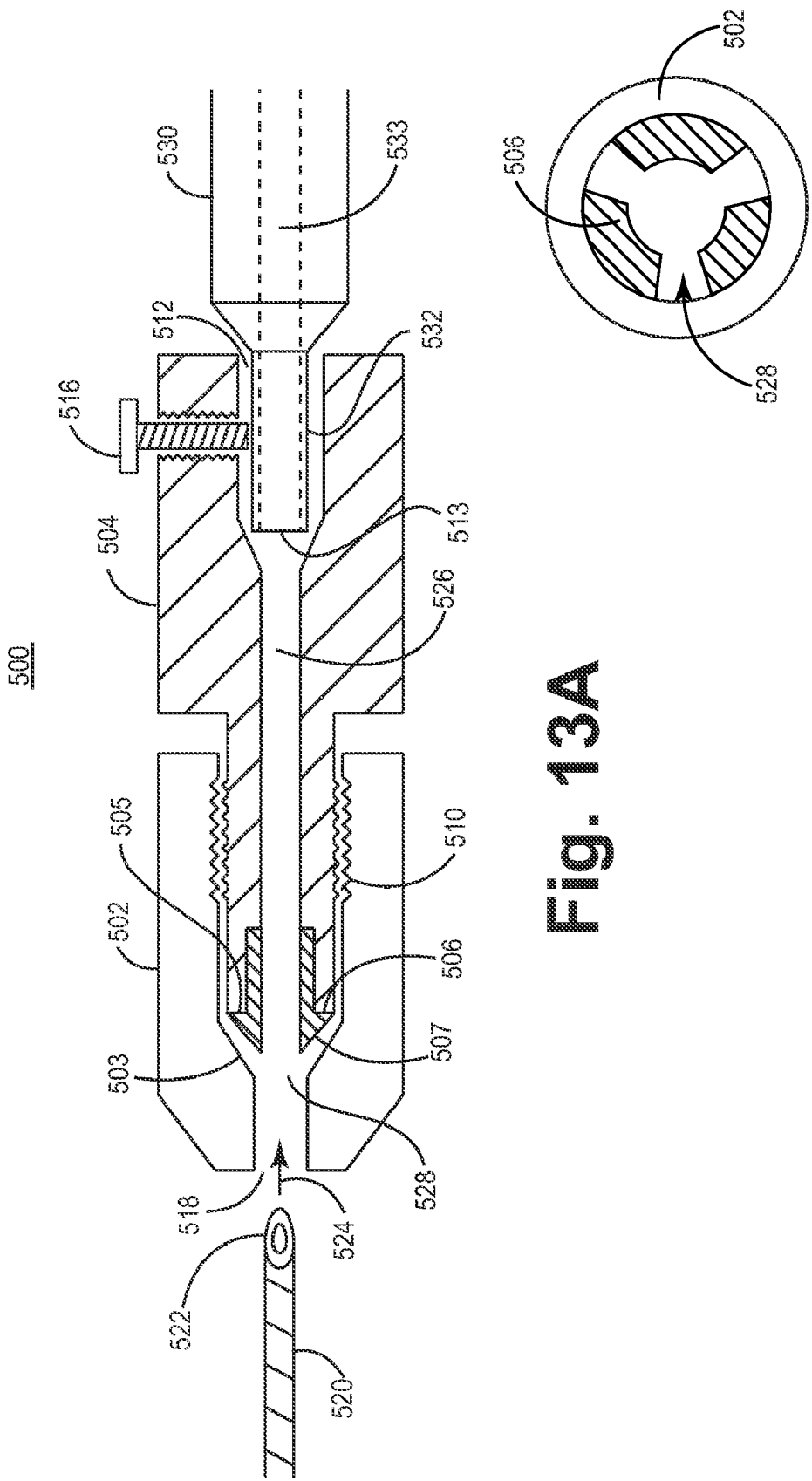
FIG. 13A is a sectional view of a locking mechanism according to one embodiment of the present invention.
FIG. 13B is a proximal end view of the locking mechanism of FIG. 13A.

FIG. 13A is a sectional view of a locking mechanism 500 according to one embodiment of the present invention and FIG. 13B is a proximal end view of locking mechanism 500. According to the illustrated embodiment, mechanism 500 is adapted hold a hollow fluid delivery device 520 in a stable position relative to a lead 530 once device 520 is passed through proximal port 513 of lead 530 and advanced a desired distance through a lumen 533 of lead 530. FIG. 13A illustrates locking mechanism 500 including a lead-clamping portion 504 and a device-clamping portion 502; wherein lead-clamping portion 504 is generally tubular forming a lumen 526 having a distal opening 512 adapted to receive a proximal connector pin 532 of lead 530 and device-clamping portion 502 is generally tubular forming a lumen 528 having a proximal opening 518 adapted to receive fluid delivery device 520. FIG. 13A further illustrates connector pin 532 inserted within lumen 526 and device-clamping portion 502 rotatably coupled to lead-clamping portion 504, via a threaded interface 510, such that lumen 526 is aligned with lumen 528 to allow fluid delivery device 520 to be passed through device-clamping portion 502 via lumen 528 in the direction of arrow 524, further through lead clamping portion 504 via lumen 526, into hollow connector pin 532 and through lumen 533 of lead 530. Although FIG. 13A illustrates a set-screw 516 as means to secure connector pin 532 in lumen 526, alternate embodiments of the present invention include any suitable securing means known to those skilled in the art, examples of which include but are not limited to press fits and clamp and clip mechanisms; furthermore lead securing means need not hold connector pin 532 but may hold any portion of a proximal end of lead 530. According to one embodiment, set-screw 516 is electrically conductive, serving to couple an electrical clip or probe to connector pin 532 such that electrical measurements can be made or pacing pulses delivered through connector pin 532, which is coupled to a lead electrode via a conductor (not shown).

FIGS. 13A–BA further illustrate locking mechanism 500 including a securing mechanism 506 formed as a chuck which fixedly engages device 520 upon rotating device-clamping portion 502 with respect to lead-clamping portion 504; angled flanges 507 of securing mechanism 506 are trapped between a proximal face 505 of lead-clamping portion 504 and an angled face 503 formed on an inner diameter of device-clamping portion 502. As device-clamping portion 502 is rotated with respect to lead clamping portion 504, angled face 503 of device-clamping portion 502 presses angled flanges 507 of securing mechanism 506 thereby causing securing mechanism 506 to squeeze inward, becoming fixedly engaged about device 520.

In a method, according to one embodiment of the present invention, connector pin 532 of lead 530 is first inserted into lumen 526 of lead-clamping portion 504 and set-screw 526 is tightened down onto connector pin 532 to secure connector pin 532 in place. Then, with securing mechanism 506 in an open position, fluid delivery device 520 is advanced through proximal locking mechanism 500 in the direction of arrow 524, into proximal port 513 and through lead lumen 533 until a distal tip 522 of device 520 exits a distal port, for example distal port 463 illustrated in FIG. 12, of lead 530. Once device distal tip 522 is positioned in a desired location, device-clamping portion 502 is rotated with respect to lead-clamping portion 504 such that securing mechanism 506 fixedly engages device 520. In this way, the position of device 520 with respect to lead 530 is stabilized and, since lead 530 includes a fixation element, for example element 461 illustrated in FIG. 12, holding the position of lead 530 stable relative to a targeted tissue site, device 520 is also held in a stable position relative to the targeted tissue site for delivery of a fluid through device 520. After delivering the fluid, device-clamping portion 502 may be rotated in an opposite direction relative to lead-clamping portion 504 to release device 520 for removal from lead lumen 533 and device-locking mechanism 500. Set-screw 516 may then be loosened to allow removal of locking mechanism 500 from connector pin 532 so that connector pin 532 may then be plugged into a medical device.

Figure 14:
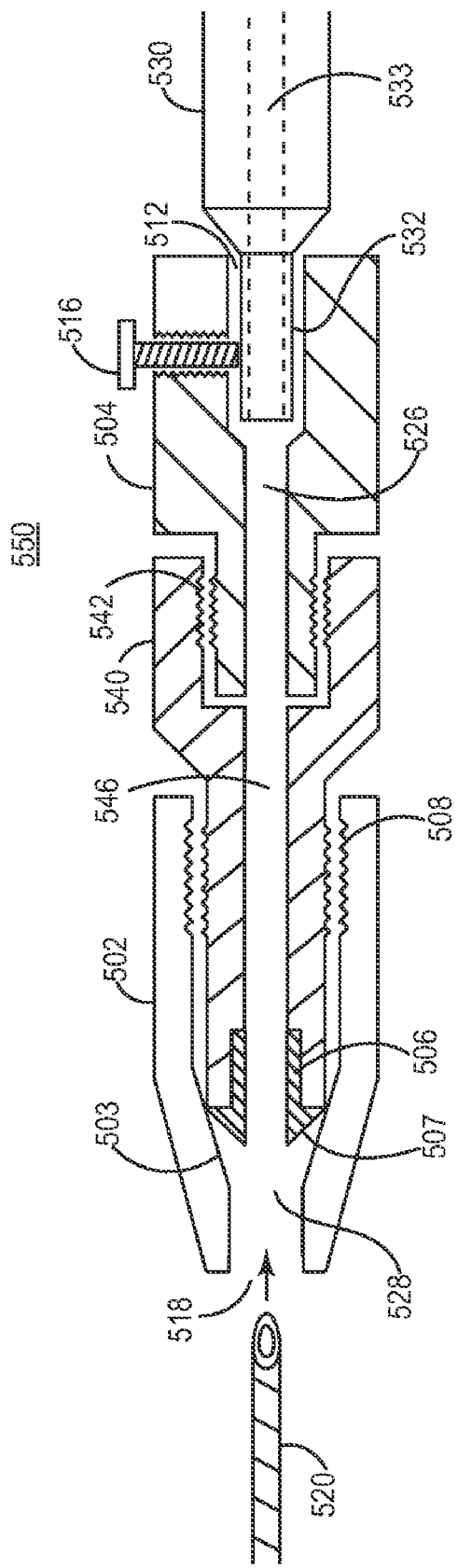
FIG. 14 is a sectional view of an alternative embodiment of a locking mechanism.
Figure 15:
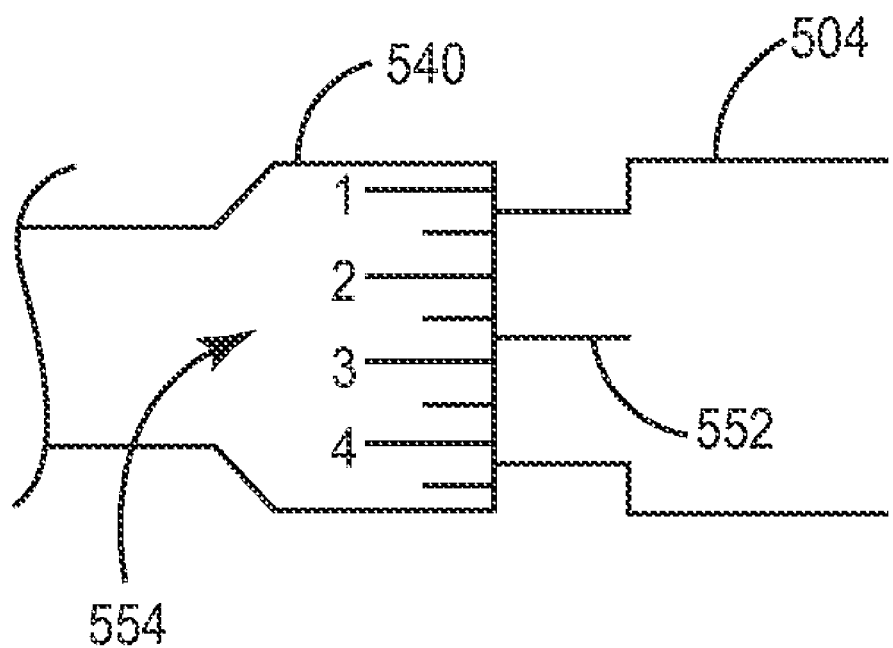
FIG. 15 is a plan view of a portion of the locking mechanism shown in FIG. 14 according to one embodiment.

FIG. 14 is a sectional view of an alternative embodiment of a locking mechanism 550 and FIG. 15 is a plan view of a portion of locking mechanism 550 according to one embodiment. Components included in locking mechanism 550 of FIG. 14 correspond to identically labeled components included in mechanism 500 of FIG. 13A. However, FIGS. 14 and 15 illustrate locking mechanism 550 including a depth adjustment portion 540, which is rotatably coupled in between lead-clamping portion 504 and device-clamping portion 502 via a first threaded interface 542 with lead-clamping portion 504 and a second threaded interface 508 with device-clamping portion 502. According to the illustrated embodiment, depth adjustment portion 540 includes an inner lumen 546 communicating with inner lumen 528 of device-clamping portion 502 and with inner lumen 526 of lead-clamping portion 504 such that a continuous lumen is formed for passage of fluid delivery device 520 in the direction of arrow 518 into lumen 533 of lead 530. In this embodiment, device securing mechanism 506 is located on the inner diameter of depth adjustment portion 540 such that when device 520 is positioned within lead lumen 533, device-clamping portion 502 may be rotated with respect to depth adjustment portion 540 to fixedly engage device 520 in device securing mechanism 506, thus stabilizing the position of device 520 with respect to lead 530. Furthermore, according to the illustrated embodiment, once secured, device 520 may be advanced or retracted in a controlled manner with respect to lead 530 by rotating depth adjustment portion 540 with respect to lead-clamping portion 504. FIG. 15 illustrates locking mechanism 550 including a reference line 552 positioned on lead-clamping portion 504 and calibrated markings 554 positioned on depth adjustment portion 540 indicating a position of device 520 with respect to lead 530 when device 520 is advanced or retracted by rotation of depth adjustment portion 540 relative to lead clamping portion 504.

Figure 16:
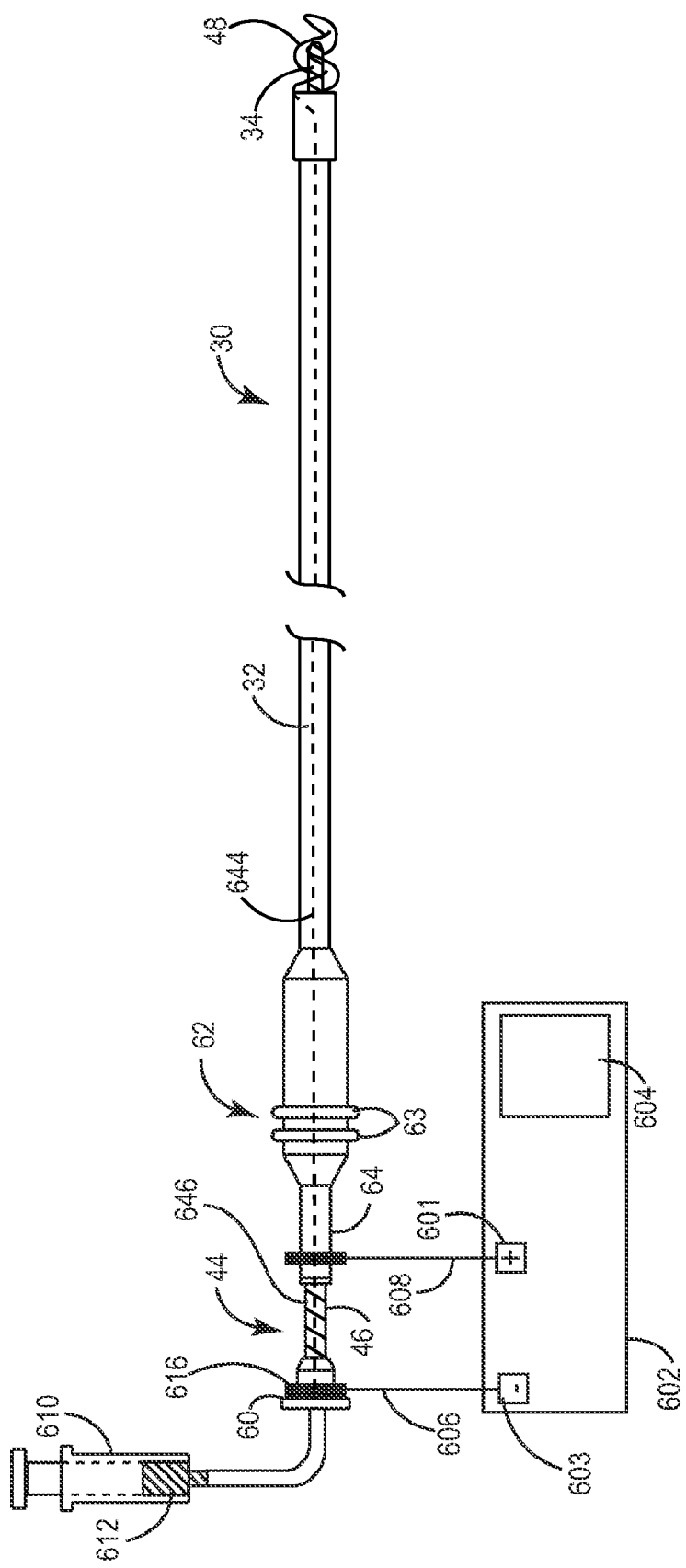
FIG. 16 is a plan view of a fluid delivery system shown including an impedance monitoring apparatus according to one embodiment of the present invention.

FIG. 16 is a plan view of a fluid delivery system shown including an impedance monitoring apparatus 602 according to one embodiment of the present invention. Medical lead 30 and fluid delivery device 44 shown in FIG. 16 generally corresponds to the system described previously in conjunction with FIG. 4A. According to the embodiment illustrated in FIG. 16, impedance monitoring apparatus 602 is coupled to medical lead 30 and fluid delivery device 44 to monitor for changes in tissue impedance upon injection of a fluid through device 44, thus providing feedback indicating when tip 48 of fluid delivery device 44 is within a targeted tissue, rather than, for example, still within a blood volume.

FIG. 16 illustrates apparatus 602 including a first terminal 601 electrically coupled, via a conductive cable 608, to lead connector pin 64, which is electrically coupled to fixation element 34 via an electrical conductor 644, and a second terminal 603 electrically coupled, via cable 606, to a proximal contact 616 of fluid delivery device 44, which is either formed of an electrically conductive material or includes an electrically conductive element 646 extending from contact 616 to tip 48. According to one method of the present invention, after advancing fluid delivery device 44 to a targeted tissue site, a bolus of fluid 612 is injected through fluid delivery device 44 via a dispensing device 610, shown here as a syringe (alternately, a fluid pump or other fluid dispensing device may be used), and an impedance is measured by apparatus 602; measured impedance is displayed on an associated display 604, which may be a graphical or digital display. Fluid 612 preferably is a solution that will cause a change in measured tissue impedance when injected into a targeted tissue, such as a solution containing electrolytes, e.g. a saline solution.

Figure 17:
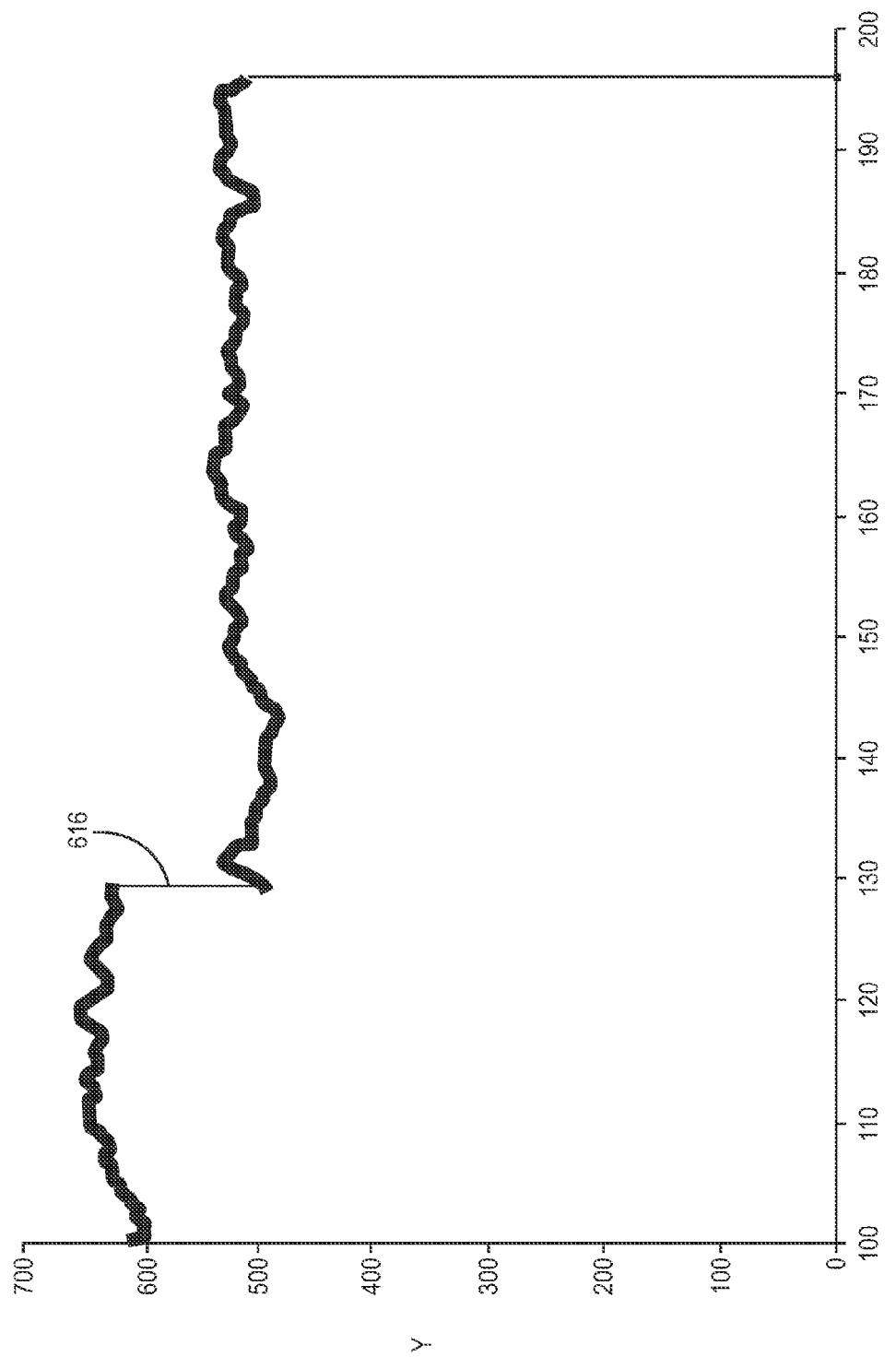
FIG. 17 is an exemplary plot of tissue impedance measured between a medical lead and a fluid delivery device.

FIG. 17 is an exemplary plot of tissue impedance measured between a medical lead electrode and a fluid delivery device. FIG. 17 illustrates impedance in ohms, along the y-axis, versus time in seconds, along the x-axis, measured when a bolus of saline solution was injected through the fluid delivery device whose tip was positioned approximately 5 mm from the lead electrode in the left ventricular epicardium of an anesthetized canine. Initial tissue impedance, prior to saline solution injection, was approximately 600 ohms. At time 616, when 100 microliters of a 0.9% NaCl solution was injected from the fluid delivery device, the tissue impedance was observed to drop abruptly to approximately 500 Ohms. After approximately one minute, the impedance is still lower than the pre-injection impedance. If the device had not been fully advanced within the tissue, such that the saline solution was injected primarily into a blood volume or leaked quickly from the tissue back into the blood volume, the impedance would be expected to return quickly to the pre-injection impedance as the fluid diffuses away quickly in the blood volume. Therefore, by monitoring impedance during injection of an electrolyte solution or other impedance-altering solution, the position of the tip of a fluid delivery device within a targeted tissue may be ascertained based on the impedance response.

Figure 18:
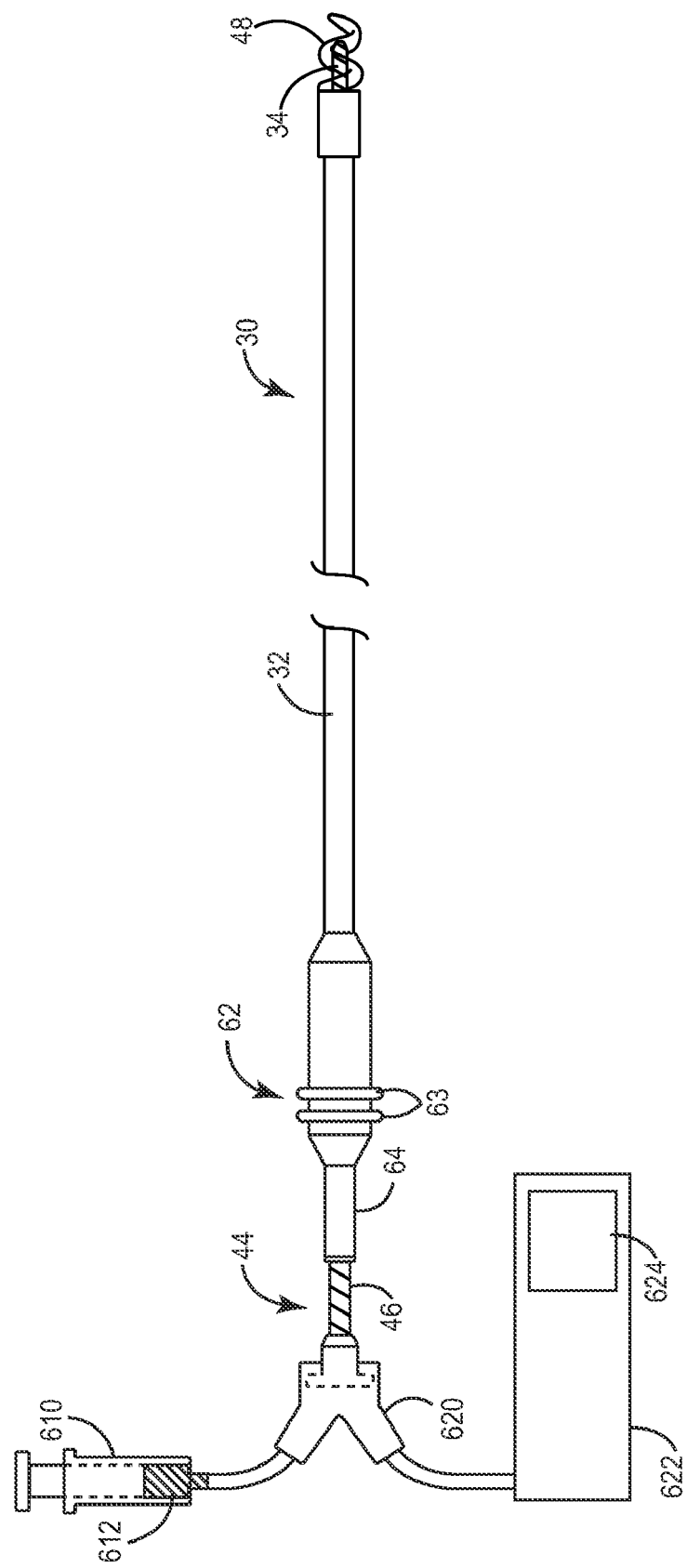
FIG. 18 is a plan view of a fluid delivery system including a pressure monitoring apparatus according to an alternate embodiment of the present invention.
Figure 19:
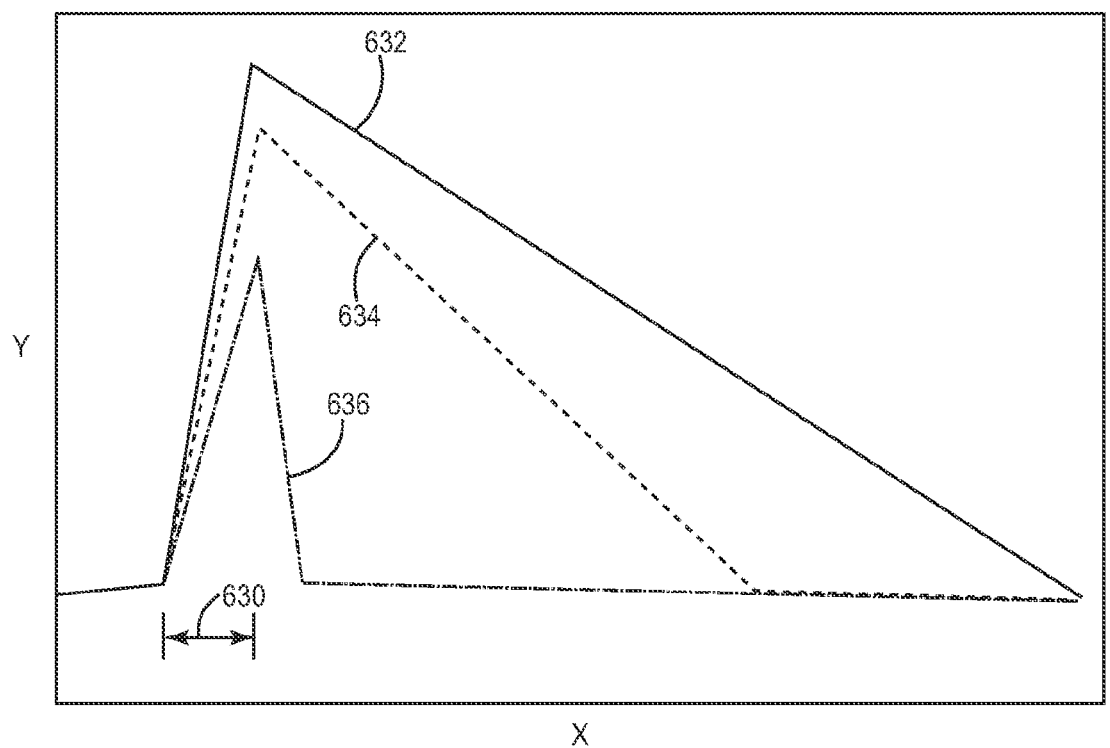
FIG. 19 is an exemplary plot of pressure changes expected to be measured by the monitoring apparatus shown in FIG. 18.

FIG. 18 is a plan view of a fluid delivery system including a pressure monitoring apparatus 622 according to an alternate embodiment of the present invention and FIG. 19 is an exemplary plot of pressure changes expected to be measured by monitoring apparatus 622. FIG. 18 illustrates pressure monitoring apparatus 622 and a fluid dispensing device 610 coupled to fluid delivery device 44 via a "Y" connector 620. According to the illustrated embodiment, when a bolus of fluid 612 is injected through fluid delivery device 44, by fluid dispensing device 610, the fluid pressure in fluid delivery device 44 is measured by pressure monitor 622 and displayed, graphically or digitally, on an associated display 624. FIG. 19 illustrates pressure plotted on the y-axis versus time on the x-axis during and after fluid injection through a fluid delivery device, for example device 44; fluid injection occurs over an interval 630. A first curve 632, representing pressure when the tip of the fluid delivery device is well-inserted into a targeted tissue, shows a sharp rise in pressure occurring during injection interval 630 followed by a slow decline in pressure thereafter as the fluid slowly diffuses through the tissue. A second curve 634, representing pressure when the tip of the fluid delivery device is partially inserted in the tissue, shows a sharp rise in pressure during the injection interval 630, but the peak pressure reached is lower than when the device is fully inserted (curve 632) since injected fluid only partially enters the tissue, leaking into the surrounding blood volume; the fall in pressure illustrated by curve 634 is also more rapid than curve 632 as the fluid more quickly diffuses at least partially out into the blood volume. A third curve 636, representing pressure when the tip of the fluid delivery device is not inserted into tissue but remains in the blood volume, shows a small rise in pressure during injection interval 630, but the developed pressure declines rapidly after injection as the fluid quickly diffuses in the blood volume.

Figure 20:
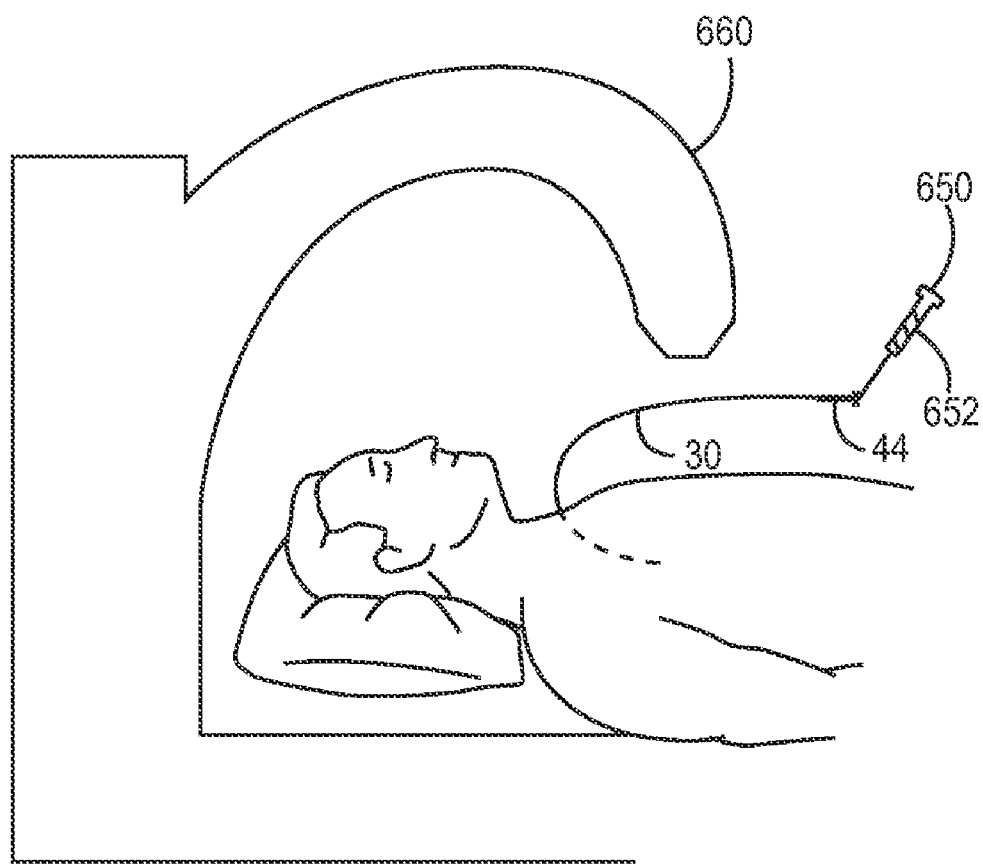
FIG. 20 is a schematic of a fluid delivery system inserted into a patient in conjunction with an imaging apparatus that may be used for monitoring.
Figure 21:
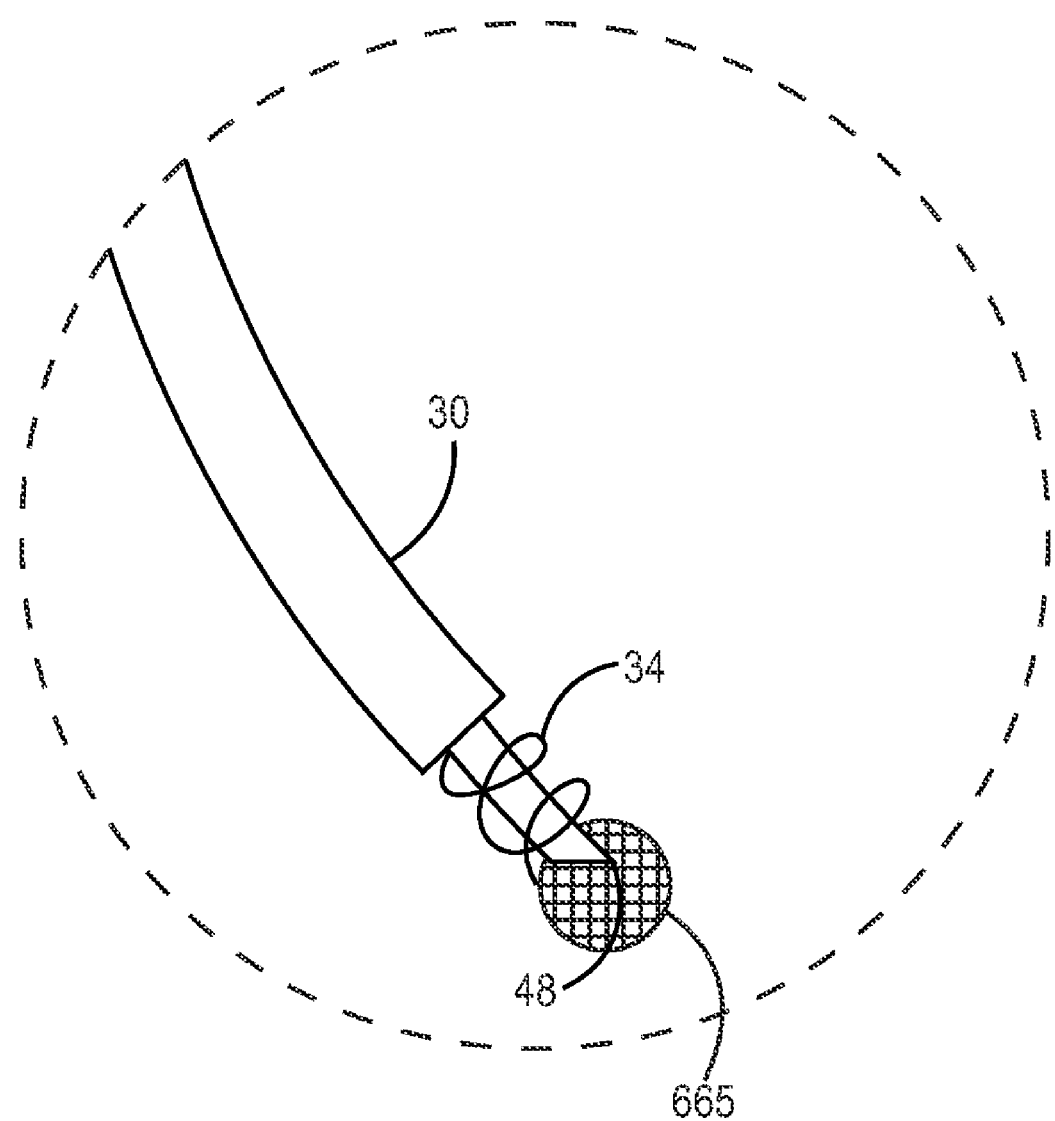
FIG. 21 is a schematic of a radiographic image that may be taken by the imaging apparatus of FIG. 20 during injection of a bolus of radio-opaque fluid through the fluid delivery system.

FIG. 20 is a schematic of a fluid delivery system inserted into a patient in conjunction with an imaging apparatus 660 that may be used for monitoring and FIG. 21 is a schematic of a radiographic image that may be taken by imaging apparatus 660 during injection of a bolus of radio-opaque fluid 652. FIG. 20 illustrates the fluid delivery system including lead 30, fluid delivery device 44 and a fluid dispensing device 650 adapted to inject bolus of radio-opaque fluid 652, for example an Isovue™ or Hypaque™ contrast agent or a combination thereof, through the fluid delivery device. According to an embodiment of the present invention, imaging apparatus 660 is a fluoroscope used to monitor a position of tip 48 (FIG. 18) of fluid delivery device 44 by means of radiographic images acquired during injection of the radio-opaque fluid 652. FIG. 21 illustrates an exemplary radiographic image wherein fixation element 34 of medical lead 30 and device tip 48 are generally visible along with a small, blotch 665 of radiopaque fluid 652 surrounding the device tip 48 indicating that tip 48 is inserted within tissue. The visible blotch 665 will slowly fade as radio-opaque fluid 652 diffuses through the tissue, whereas, if device tip 48 is only partially inserted into tissue or remains in the blood volume, radio-opaque fluid 652 would quickly diffuse without forming blotch 665.

Figure 22:
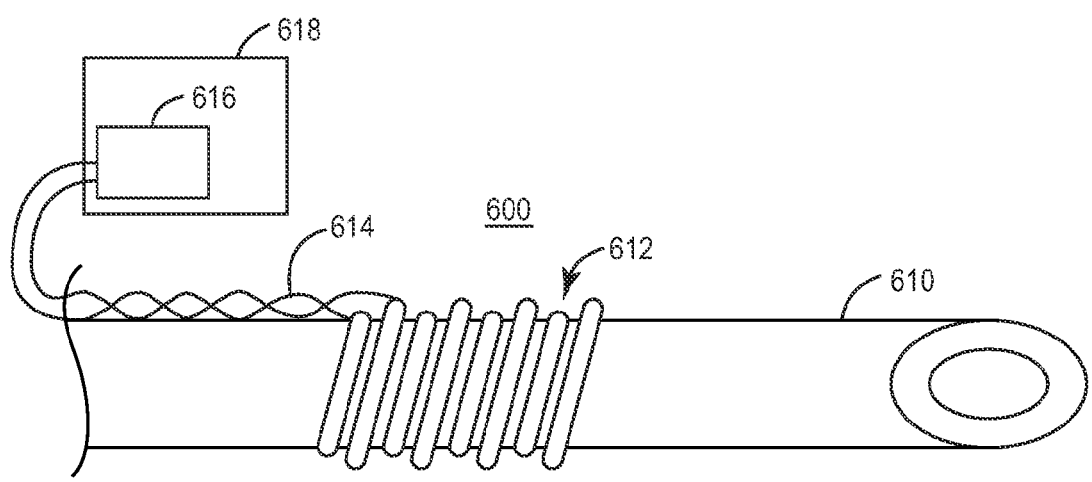
FIG. 22 is a plan view of a distal portion of a fluid delivery device according to another embodiment of the present invention.

FIG. 22 is a plan view of a distal portion of a fluid delivery device 600 according to another embodiment of the present invention. FIG. 22 illustrates device 600 including a distal portion 610 and electromagnetic receiver coils 612 wound around at least a portion of the distal portion; electromagnetic coils 612 are coupled to a twisted pair of insulated conductors 614, which deliver a magnetically induced current from electromagnetic coils 612 to a signal converter 616. The coils may be encased in a polymer coating, for example a polyester heat shrink tubing, to protect and electrically insulate the coils from other components. According to an embodiment of the present invention, fluid delivery device 600 is used in conjunction with electromagnetic imaging apparatus 618, which can monitor the location of the fluid delivery device tip relative to a targeted tissue. For example, magnetic resonance imaging may be used to visualize the location of distal portion 610 relative to imaged tissue structures; alternatively, methods for tracking an instrument within the human body using electromagnetic localization methods may be useful for tracking the location of the distal portion 610 as it is advanced to a targeted tissue site. Location mapping systems that may be used for tracking a medical device in a patient's body are generally disclosed in U.S. Pat. No. 5,983,126 issued to Wittkampf and U.S. Pat. No. 6,236,875 issued to Bucholz et al., both patents incorporated herein by reference in their entirety. It should be noted that, according to some embodiments of the present invention, device 600 is adapted to pass through any of the previously described leads, for example leads 401, 460, 530 and 30, according to the methods previously described for other embodiments of fluid delivery devices.

Methods for monitoring a location of a fluid delivery device within a tissue described herein may be utilized with any of the various embodiments of medical lead and fluid delivery systems described herein. Furthermore, it is recognized that numerous variations of methods for measuring a biochemical, bioelectrical, or biomechanical change in the tissue or in the tissue response to excitation during or after injection of a fluid may be conceived for use in verifying the fluid delivery device is well-inserted in a targeted tissue. Additionally modifications to imaging methods described herein and various imaging techniques may be conceived for visualizing the injected fluid and/or the fluid delivery device tip relative to a targeted tissue site. Furthermore, although various embodiments described herein include an implantable medical lead, the inventive system may also be used in procedures for treating a volume of tissue in which chronic implantation of a lead is not required. For example, other therapy modalities, which may benefit from the inventive system and do not require chronic implantation of a lead include treatment of myocardial infarction via cell delivery and treatment of coronary artery disease via drugs or biologic agents such as angiogenic factors. While the embodiments described herein have been described with regard to cardiac leads and the treatment of cardiac tissue, aspects of the inventive system may also be used in regard to other types of leads and other types of bodily tissue, such as kidney, brain, pancreas, or other organs or tissues. The described embodiments are therefore exemplary and should not be considered limiting with regard to the following claims.

The invention claimed is:

1. A medical fluid delivery system, comprising
an implantable medical lead including a proximal port, a distal port, a lumen extending between the proximal port and the distal port and a distal fixation element adapted to secure the lead to a tissue site such that the distal port is in proximity to the tissue site; and
a fluid delivery device adapted to pass through the lead proximal port, through the lead lumen and through the lead distal port, the device including a tissue piercing distal tip and a pre-formed curve in proximity to the distal tip such that the tip is directed away from the fixation element after passing beyond the distal port of the lead.

2. The system of claim 1, wherein:
the implantable medical lead further includes a coiled conductor forming a portion of the lumen;
the device distal tip includes a beveled end; and
the coiled conductor includes a one or more filars having a pitch adapted to prevent the beveled end of the distal tip from catching in the coil as the device passes through the lumen.

3. A medical fluid delivery system, comprising:
an implantable medical lead including a proximal port, a distal port, a lumen extending between the proximal port and the distal port and a distal fixation element adapted to secure the lead to a tissue site such that the distal port is in proximity to the tissue site;
a fluid delivery device adapted to pass through the lead proximal port, through the lead lumen and through the lead distal port, the device including a tissue piercing distal tip and a pre-formed curve in proximity to the distal tip such that the tip is directed away from the fixation element after passing beyond the distal port of the lead; and
means for adjusting a position of the device distal tip with respect to the lead distal port.

4. The system of claim 3, wherein the fluid delivery device is formed of a material comprising a shape memory alloy.

5. The system of claim 3, wherein the fluid delivery device is formed from a material comprising a super-elastic material.

6. The system of claim 3, wherein the means for adjusting the position of the device distal tip comprises a threaded interface formed between the fluid delivery device and the lead lumen.

7. The system of claim 3, further comprising a locking mechanism adapted to hold the fluid delivery device in a stable position within the lead lumen and including a lead-clamping portion and a fluid delivery device-clamping portion.

8. The system of claim 7, wherein:
the implantable medical lead further includes a proximal connector pin formed about the proximal port; and
the locking mechanism is affixed to the connector pin via a set-screw.

9. The system of claim 8, wherein the set-screw forms an electrical coupling between an electrical probe and the connector pin.

10. The system of claim 7, wherein the device-clamping portion of the locking mechanism includes a chuck mechanism for engaging the device.

11. The system of claim 3, further comprising:
a locking mechanism adapted to hold the fluid delivery device in a stable position within the lead lumen and including a lead-clamping portion and a fluid delivery device-clamping portion; and
wherein the means for adjusting the position of the device distal tip comprises a threaded interface formed between the lead-clamping portion and the device-clamping portion of the locking mechanism.

12. The system of claim 3, wherein the means for adjusting the position of the device distal tip further comprises a stop limiting a maximum distance between the device distal tip and the lead distal port.

13. The system of claim 3, wherein the means for adjusting the position of the device distal tip further comprises a fluid delivery device position indicator.

14. The system of claim 3, wherein:
the implantable medical lead further includes a proximal connector pin formed about he proximal port and an elongated conductor electrically coupling the connector pin to the fixation element;
the fluid delivery device further includes a proximal end and a conductive element extending between the proximal end and the device distal tip; and
the means for adjusting the position of the device distal tip comprises an impedance monitor coupled to the connector pin of the lead and the proximal end of the needle, the impedance monitor adapted to measure an electrical impedance change between the distal tip of the device and the fixation element when the bolus of fluid is injected through the device.

15. The system of claim 3, wherein:
the fluid delivery device further includes a proximal end; and
the means for adjusting the position of the device distal tip comprises a pressure monitor coupled to the proximal end of the device and adapted to measure a pressure change when the bolus of fluid is injected through the device.

16. The system of claim 3, wherein:
the fluid delivery device further includes a distal portion, electromagnetic receiver coils wound around the distal portion and a pair of insulated conductors coupled to the receiver coils and adapted to deliver a magnetically induced current from the coils to a signal converter; and
the means for adjusting the position of the device distal tip comprises an electromagnetic imaging or mapping system including the signal converter.

17. The system of claim 3, wherein:
the implantable medical lead further includes a coiled conductor forming a portion of the lumen;
the device distal tip includes a beveled end; and
the coiled conductor includes a one or more filars having a pitch adapted to prevent the beveled end of the distal tip from catching in the coil as the device passes through the lumen.

* * * * *